US012649709B2

(12) United States Patent
Hofmann

(10) Patent No.: US 12,649,709 B2
(45) Date of Patent: Jun. 9, 2026

(54) NAPHTHOQUINONE-BASED CHALCONE DERIVATIVES AND USES THEREOF

(71) Applicant: Robert F. Hofmann, Austin, TX (US)

(72) Inventor: Robert F. Hofmann, Austin, TX (US)

( * ) Notice: Subject to any disclaimer, the term of this patent is extended or adjusted under 35 U.S.C. 154(b) by 831 days.

(21) Appl. No.: 17/908,876

(22) PCT Filed: Feb. 24, 2021

(86) PCT No.: PCT/US2021/019400
§ 371 (c)(1),
(2) Date: Sep. 1, 2022

(87) PCT Pub. No.: WO2021/173658
PCT Pub. Date: Sep. 2, 2021

(65) Prior Publication Data

US 2025/0002436 A1 Jan. 2, 2025

Related U.S. Application Data

(60) Provisional application No. 62/980,787, filed on Feb. 24, 2020.

(51) Int. Cl.
*C07C 50/38* (2006.01)
*A61K 31/122* (2006.01)
*C07C 46/06* (2006.01)

(52) U.S. Cl.
CPC ............ *C07C 50/38* (2013.01); *A61K 31/122* (2013.01); *C07C 46/06* (2013.01)

(58) Field of Classification Search
CPC ...................................................... C07C 50/38
See application file for complete search history.

(56) References Cited

U.S. PATENT DOCUMENTS

2013/0158077 A1* 6/2013 Kahrs ..................... A61P 21/02
514/342
2014/0031432 A1 1/2014 Jankowski et al.
2015/0224066 A1 8/2015 Schlievert

FOREIGN PATENT DOCUMENTS

WO 2006/107827 A1 10/2006

OTHER PUBLICATIONS

International Preliminary Report on Patentability, PCT/US2021/019400, dated Aug. 30, 2022, 6 pages.
International Search Report and Written Opinion, PCT/US2021/019400, dated Apr. 22, 2021, 8 pages.
Pubchem, SID 384567975, Available Date: Jun. 21, 2019 [retrieved on Apr. 7, 2021]. Retrieved from the Internet: <URL: https://pubchem.ncbi.nlm.nih.gov/substance/384567975>.
De Oliveira, M-R et al., "Curcumin, mitochondrialbiogenesis, and mitophagy: Exploring recent data and indicating future needs," Biotechnology Advances, vol. 34(5):813-826 (2016).
Extended European search report, EP Application No. 21760477, dated Mar. 7, 2024, 12 pages.

* cited by examiner

*Primary Examiner* — Svetlana M Ivanova
(74) *Attorney, Agent, or Firm* — NELSON MULLINS RILEY & SCARBOROUGH LLP

(57) ABSTRACT

The present disclosure provides compounds of formula 1 to inhibit or prevent mitochondrial dysfunction by augmenting mitochondrial function. Mitochondrial dysfunction is the hallmark of a wide range of diseases and disorders. Mitochondria are a promising therapeutic target for the detection, prevention and treatment of various human diseases such as cancer, neurodegenerative diseases, ischemia-reperfusion injury, diabetes and obesity.

13 Claims, 23 Drawing Sheets

Dimendione Curcuminoid
RLS6

RLS6 Enol

RLS5
Compound 1.A
SNC1 (RLS5 formulated in PEG200)

RLS4
Compound 1.B

RLS3

RLS2

Analogue of RLS6
Compound 2.A

Analogue of RLS4
Compound 2.B

Analogue of RLS6
Compound 3.A

Analogue of RLS4
Compound 3.B

NAPHTHOQUINONE-BASED CHALCONE DERIVATIVES AND USES THEREOF

CROSS REFERENCE TO RELATED APPLICATIONS

This application is a 35 U.S.C. 371 national stage filing of International Application No. PCT/US2021/019400, filed on Feb. 24, 2021, which claims priority to U.S. Provisional Patent Application No. 62/980,787, filed Feb. 24, 2020, the disclosures of which are incorporated by reference herein in its entirety.

FIELD

The present disclosure relates to compounds that can increase the stabilization of the mitochondrial electron transport chain consisting of naphthoquinone-based chalcone derivatives for use as compounds in pharmaceutical compositions and formulations.

BACKGROUND

The concerns of pesticides and other environmental toxins are of increasing importance to the fields of restorative medicine. Pesticides with core synthetic kernel structures, such as synthetic phosphonates, halogenated cyclobenzenes, or dioxins, are difficult to fully metabolize once cellularly integrated into mitochondria.

Mitochondria are membrane-enclosed organelles found in the cytoplasm of eukaryotic cells and their crucial function is to generate energy in the form of ATP through oxidative phosphorylation via the Electron Transport Chain (ETC). Damage to the mitochondrial ETC and Adenosine-5'-Triphosphate (ATP) production causes inflammatory stress, proteomic deregulation and mitochondrial dysfunction. Mitochondrial dysfunction is the hallmark of a wide range of diseases and disorders (Nicolson, G. L. Integrative Medicine. 13, pp 35-43, 2014).

Curcumin is a well-known polyphenolic compound used as a dietary anti-inflammatory and chemopreventive agent. Curcumin is an abundant component of turmeric and consists of two methoxyphenol rings connected by a conjugated heptadienedione chain. The promising role of curcumin against different diseases has been highly publicized but it is unstable at physiological pH and rapidly degrades in an autoxidation reaction to a major bicyclopentadione product in which the 7-carbon chain has undergone oxygenation and double cyclization (Gordon, O. N. et al, J. Biol. Chem. 290, pp 4817-4828, 2015).

The present disclosure describes more highly conjugated and resonantly energetic redox analogs to the curcumin natural substance to enable the complete metabolism of pesticides and toxins within human/animal cells, extracorporeal mitochondrial transplants, food chain plants, or polluted biomes. The bio-electronics model of the mitochondrial inner membrane has a two-part ATPase that acts as a proton pump in a recycling fuel cell. The compounds of the present disclosure act like redox molecules with planar-like components in a biological current-producing Synchrocyclotron of rotating capacitor discs, along with metal-chelated porphyrins. This Synchrocyclotron model places all functions for ETC repair and ATP augmentation into one compound targeted to mitochondria.

The errors in metabolic, genetic, protein synthesis and ATP related energetic functions of mitochondria due to the substitution of a synthetic Phosphonate molecule for organic Phosphate are protean. Phosphonates are organic phosphorous compounds characterized by a stable carbon to phosphorous bond (C—P) which usually resists biochemical, thermal and photochemical decomposition. The mere reorganization of COP in phosphate to CPO in phosphonate is the kernel to the downstream pathology. It is desirable to overwhelm this pathology with enhanced porphyrin to quinone redox activity, if not the direct dismutation of the phosphonate molecule directly back to phosphate.

Mitochondria are a promising therapeutic target for the detection, prevention and treatment of various human diseases such as cancer, neurodegenerative diseases (including neurodementia, Alzheimer's Disease, Parkinson's Disease and Amyotrophic Lateral Sclerosis or ALS), ischemia-reperfusion injury, diabetes and obesity. It is desirable to provide alternative compounds capable of inhibiting or preventing mitochondrial dysfunction by augmenting mitochondrial function.

BRIEF SUMMARY OF THE INVENTION

Generally, the present disclosure provides menadione derivatives, for example compounds and compositions which are capable of treating or preventing mitochondrial dysfunction and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition or prevention of classical mitochondrial dysfunction in humans.

In one aspect is a compound having the structure of Formula (I):

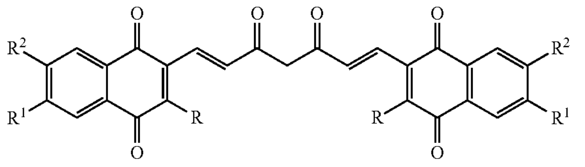

wherein:

R is selected from —H, —$CH_3$, —$C_2H_5$, alkyl —$C_nH_2$n+1 (where n is an integer from 3-x), or —OH;

R1 is selected from —H, —$CH_3$, —$C_2H_5$, —$OCH_3$, alkyl —$C_nH_2$n+1 (where n is an integer from 3-x), —OH, phenyl —$C_6H_5$, naphthyl, or amino acid; and R2 is selected from —H, —$CH_3$, —$C_2H_5$, —$OCH_3$, alkyl —$C_nH_2$n+1 (where n is an integer from 3-x), —OH, phenyl —$C_6H_5$, naphthyl, or amino acid.

The compounds disclosed herein, alone or in combination with each other, can be used in the form of a pharmaceutical composition, for example, in solid, semisolid, or liquid form, which includes one or more of a disclosed compound, as an active ingredient, in a mixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active compound is included in the pharmaceutical composition in an amount sufficient to produce the desired effect upon the process or condition of the disease.

The compounds disclosed herein, alone or in combination with each other, can be used encapsulated in a vector, such as a macro-, micro- or nano-capsule, a liposome or a liposome-like vesicle; or included in a macro, micro- or nano-particle such as a biodegradable polymeric particle.

The compounds disclosed herein, alone or in combination with each other, can be used in pro-drug form wherein an amino acid residue, or polypeptide chain of two or more (eg., two, three or four) amino acid residues is covalently joined through an amide or ester bond to a free amino, hydroxy or carboxylic acid group of the compounds.

The compounds disclosed herein, alone or in combination with each other, can be used in combination therapies, co-administering a disclosed compound and an additional active agent, as part of a specific treatment regimen intended to provide beneficial effect from the co-action of these therapeutic agents.

The compounds disclosed herein, inhibit or prevent mitochondrial dysfunction, comprising administering a therapeutically effective amount of a compound of Formula (I), or a solvate, hydrate, tautomer, N-oxide, stereoisomer, or a pharmaceutically acceptable salt thereof, to a patient in need thereof to inhibit or prevent mitochondrial dysfunction.

The compounds disclosed herein, are administered to patients in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration include subcutaneous injections, intravenous or intramuscular injections or infusion techniques.

The compounds disclosed herein, can be used in combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

Other aspects and features of the present disclosure will become apparent to those ordinarily skilled in the art upon review of the following description of specific embodiments in conjunction with the accompanying figures.

In the following description, for purposes of explanation, numerous details are set forth in order to provide a thorough understanding of the examples. However, it will be apparent to one skilled in the art that these specific details are not required.

BRIEF DESCRIPTION OF THE DRAWINGS

Embodiments of the present disclosure will now be described, by way of example only, with reference to the attached Figures.

DETAILED DESCRIPTION OF THE INVENTION

Figure 1:
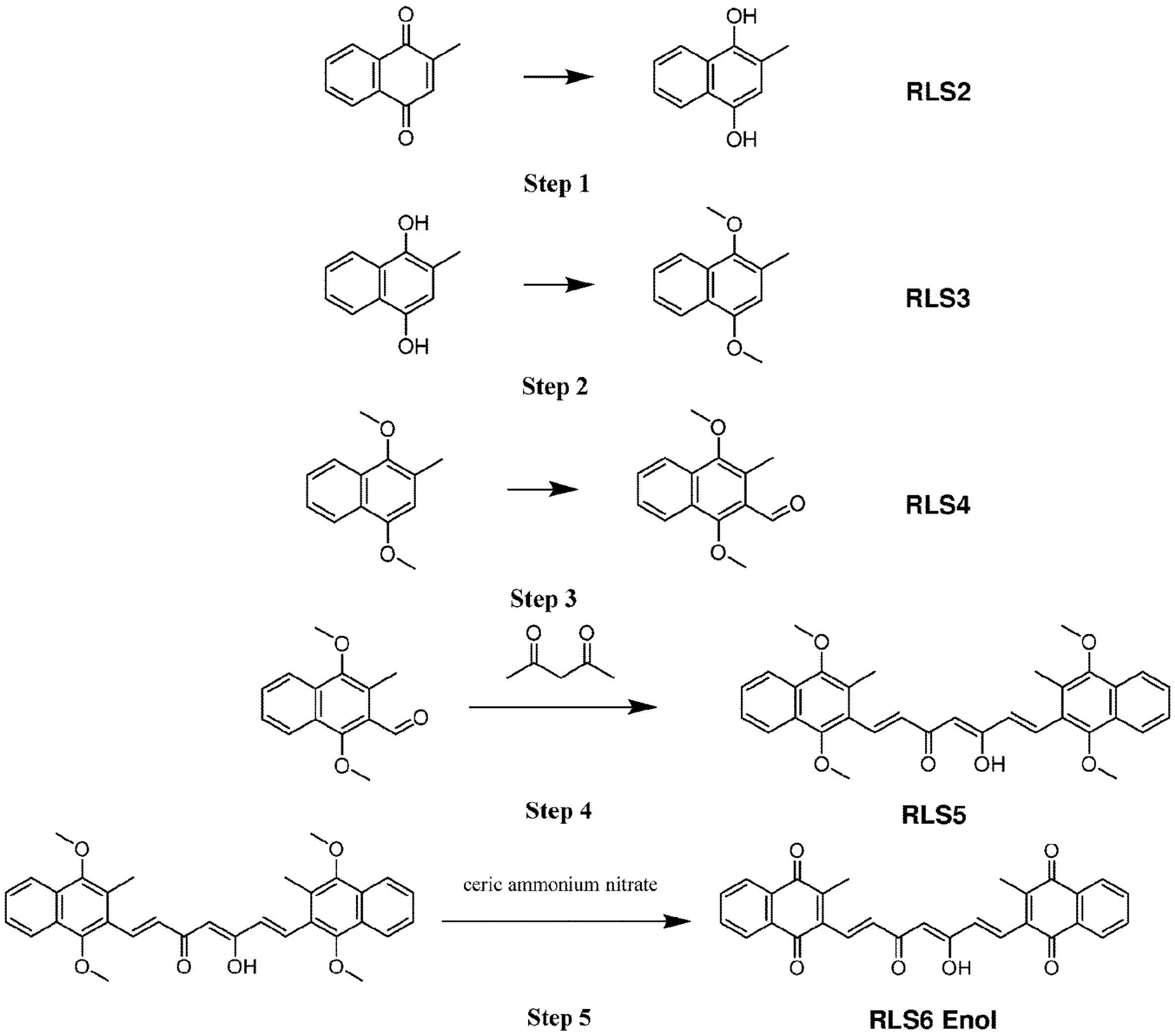
FIG. 1 shows a synthetic pathway for an exemplary compound of formula 1.

This disclosure is directed, at least in part, to compounds and compositions that can treat or prevent mitochondrial dysfunction. In some embodiments, provided herein are compounds capable of inhibiting or preventing mitochondrial dysfunction by acting as a synthetic co-factor or engineered biomimetic factor. In some embodiments, provided herein are compounds capable of tightly targeting mitochondria function that will inhibit or prevent mitochondrial dysfunction, thereby generating important novel possibilities for treatment of disease resulting from mitochondrial dysfunction.

Mitochondria are dynamic double-membrane bound organelles which have key roles in a variety of cellular functions such as energy producing, regulation of calcium flux, cellular stress responses including autophagy and apoptosis (De Oliveira, M. R, et al., Biotechnology Advances 34, pp 813-826, 2016). A growing body of evidence indicates that mitochondrial dysfunction is the main etiological factor in a myriad of diseases.

Mitochondrial dysfunction is characterized by a loss of efficiency in the ETC and reductions in the synthesis of high-energy molecules, such as ATP, and is characteristic of aging, and essentially, of all chronic diseases (Swerdlow, R. H., et al., Biochim Biophys Acta 1812, pp 1630-1639, 2011; Reddy, P. H. Neuromolecular Med. 10, pp 291-315, 2008; Green, D. R, et al., Science 333, pp 1109-1112, 2011; Reddy, P. H, et al., Curr Alzheimer Res 8, pp 393-409, 2011). These diseases include neurodegenerative diseases, Alzheimer's disease, Parkinson's disease, Huntington's disease amyotrophic lateral sclerosis, and Friedreich's ataxia; cardiovascular diseases, such as atherosclerosis and other heart and vascular conditions; diabetes and metabolic syndrome; autoimmune diseases, such as multiple sclerosis, systemic lupus erythematosus, and type 1 diabetes; neurobehavioral and psychiatric diseases, such as autism spectrum disorders, schizophrenia, and bipolar and mood disorders; gastrointestinal disorders; fatiguing illnesses, such as chronic fatigue syndrome and Gulf War illnesses; musculoskeletal diseases, such as fibromyalgia and skeletal muscle hypertrophy/atrophy; cancer; and chronic infections.

Curcumin is a well-known polyphenolic compound used as a dietary anti-inflammatory and chemopreventive agent. Curcumin is an abundant component of turmeric and consists of two methoxyphenol rings connected by a conjugated heptadienedione chain. The promising role of curcumin against different diseases has been highly publicized but it is unstable at physiological pH and rapidly degrades in an autoxidation reaction to a major bicyclopentadione product in which the 7-carbon chain has undergone oxygenation and double cyclization (Gordon, O. N, et al, J. Biol. Chem. 290, pp 4817-4828, 2015).

The present disclosure describes more highly conjugated and resonantly energetic redox analogs to the curcumin natural substance to enable the complete metabolism of pesticides and toxins within human/animal cells, extracorporeal mitochondrial transplants, food chain plants, or polluted biomes. The bio-electronics model of the mitochondrial inner membrane has a two-part ATPase that acts as a proton pump in a recycling fuel cell. The compounds of the present disclosure act like redox molecules with planar-like components in a biological current-producing Synchrocyclotron of rotating capacitor discs, along with metal-chelated porphyrins. This Synchrocyclotron model places all functions for ETC repair and ATP augmentation into one compound targeted to mitochondria.

Compounds according to the present disclosure may inhibit or prevent mitochondrial dysfunction, and may be effective in retarding the disease process. Generally, the present disclosure provides compounds according to formula 1 wherein: R is selected from —H, —$CH_3$, —$C_2H_5$, alkyl —$C_nH_2n+1$ (where n is an integer from 3-x), or —OH; R1 is selected from —H, —$CH_3$, —$C_2H_5$, —$OCH_3$, alkyl —$C_nH_2n+1$ (where n is an integer from 3-x), —OH, phenyl —$C_6H_5$, naphthyl, or amino acid; and R2 is selected from —H, —$CH_3$, —$C_2H_5$, —$OCH_3$, alkyl —$C_nH_2n+1$ (where n is an integer from 3-x), —OH, phenyl —$C_6H_5$, naphthyl, or amino acid.

In some examples, R, R1 and R2 are all the same such as —H, —$CH_3$, —$C_2H_5$, —OH.

Preferably, compounds according to the present disclosure have R being different from R1 and R2 while R1 and R2 are the same.

In preferred compounds R is —$CH_3$ and R1 and R2 are the same.

In another specific example, there is provided a naphthoquinone-based chalcone compound having R selected from —H, and R1 and R2 selected from —H.

In another specific example, there is provided a naphthoquinone-based chalcone compound having R selected from —H, and R1 and R2 selected from —$CH_3$.

In another specific example, there is provided a naphthoquinone-based chalcone compound having R selected from —H, and R1 and R2 selected from —$C_2H_5$.

In another specific example, there is provided a naphthoquinone-based chalcone compound having R selected from —H, and R1 and R2 selected from —$OCH_3$.

In another specific example, there is provided a naphthoquinone-based chalcone compound having R selected from —H, and R1 and R2 selected from alkyl —$C_nH_2n+1$ (where n is an integer from 3-x).

In another specific example, there is provided a naphthoquinone-based chalcone compound having R selected from —H, and R1 and R2 selected from —OH.

In another specific example, there is provided a naphthoquinone-based chalcone compound having R selected from —H, and R1 and R2 selected from phenyl —$C_6H_5$.

In another specific example, there is provided a naphthoquinone-based chalcone compound having R selected from —H, and R1 and R2 selected from naphthyl.

In another specific example, there is provided a naphthoquinone-based chalcone compound having R selected from —H, and R1 and R2 selected from an amino acid.

In one specific example, there is provided a naphthoquinone-based chalcone compound having R selected from —$CH_3$, and R1 and R2 selected from —H.

In another specific example, there is provided a naphthoquinone-based chalcone compound having R selected from —$CH_3$, and R1 and R2 selected from —$CH_3$.

In another specific example, there is provided a naphthoquinone-based chalcone compound having R selected from —$CH_3$, and R1 and R2 selected from —$C_2H_5$.

In another specific example, there is provided a naphthoquinone-based chalcone compound having R selected from —$CH_3$, and R1 and R2 selected from —$OCH_3$.

In another specific example, there is provided a naphthoquinone-based chalcone compound having R selected from —$CH_3$, and R1 and R2 selected from alkyl —$C_nH_2n+1$ (where n is an integer from 3-x).

In another specific example, there is provided a naphthoquinone-based chalcone compound having R selected from —$CH_3$, and R1 and R2 selected from —OH.

In another specific example, there is provided a naphthoquinone-based chalcone compound having R selected from —$CH_3$, and R1 and R2 selected from phenyl —$C_6H_5$.

In another specific example, there is provided a naphthoquinone-based chalcone compound having R selected from —$CH_3$, and R1 and R2 selected from naphthyl.

In another specific example, there is provided a naphthoquinone-based chalcone compound having R selected from —$CH_3$, and R1 and R2 selected from an amino acid.

In another specific example, there is provided a naphthoquinone-based chalcone compound having R selected from —$C_2H_5$, and R1 and R2 selected from —H.

In another specific example, there is provided a naphthoquinone-based chalcone compound having R selected from —$C_2H_5$, and R1 and R2 selected from —$CH_3$.

In another specific example, there is provided a naphthoquinone-based chalcone compound having R selected from —$C_2H_5$, and R1 and R2 selected from —$C_2H_5$.

In another specific example, there is provided a naphthoquinone-based chalcone compound having R selected from —$C_2H_5$, and R1 and R2 selected from —$OCH_3$.

In another specific example, there is provided a naphthoquinone-based chalcone compound having R selected from —$C_2H_5$, and R1 and R2 selected from alkyl —$C_nH_2n+1$ (where n is an integer from 3-x).

In another specific example, there is provided a naphthoquinone-based chalcone compound having R selected from —$C_2H_5$, and R1 and R2 selected from —OH.

In another specific example, there is provided a naphthoquinone-based chalcone compound having R selected from —$C_2H_5$, and R1 and R2 selected from phenyl —$C_6H_5$.

In another specific example, there is provided a naphthoquinone-based chalcone compound having R selected from —$C_2H_5$, and R1 and R2 selected from naphthyl.

In another specific example, there is provided a naphthoquinone-based chalcone compound having R selected from —$C_2H_5$, and R1 and R2 selected from an amino acid.

In another specific example, there is provided a naphthoquinone-based chalcone compound having R selected from alkyl —$C_nH_2n+1$ (where n is an integer from 3-x), and R1 and R2 selected from —H.

In another specific example, there is provided a naphthoquinone-based chalcone compound having R selected from alkyl —$C_nH_2n+1$ (where n is an integer from 3-x), and R1 and R2 selected from —$CH_3$.

In another specific example, there is provided a naphthoquinone-based chalcone compound having R selected from alkyl —$C_nH_2n+1$ (where n is an integer from 3-x), and R1 and R2 selected from —$C_2H_5$.

In another specific example, there is provided a naphthoquinone-based chalcone compound having R selected from alkyl —$C_nH_2n+1$ (where n is an integer from 3-x), and R1 and R2 selected from —$OCH_3$.

In another specific example, there is provided a naphthoquinone-based chalcone compound having R selected from alkyl —$C_nH_2n+1$ (where n is an integer from 3-x), and R1 and R2 selected from alkyl —$C_nH_2n+1$ (where n is an integer from 3-x).

In another specific example, there is provided a naphthoquinone-based chalcone compound having R selected from alkyl —$C_nH_2n+1$ (where n is an integer from 3-x), and R1 and R2 selected from —OH.

In another specific example, there is provided a naphthoquinone-based chalcone compound having R selected from alkyl —$C_nH_2n+1$ (where n is an integer from 3-x), and R1 and R2 selected from phenyl —$C_6H_5$.

In another specific example, there is provided a naphthoquinone-based chalcone compound having R selected from alkyl —$C_nH_2n+1$ (where n is an integer from 3-x), and R1 and R2 selected from naphthyl.

In another specific example, there is provided a naphthoquinone-based chalcone compound having R selected from alkyl —$C_nH_2n+1$ (where n is an integer from 3-x), and R1 and R2 selected from an amino acid.

In another specific example, there is provided a naphthoquinone-based chalcone compound having R selected from —OH, and R1 and R2 selected from —H.

In another specific example, there is provided a naphthoquinone-based chalcone compound having R selected from —OH, and R1 and R2 selected from —$CH_3$.

In another specific example, there is provided a naphthoquinone-based chalcone compound having R selected from —OH, and R1 and R2 selected from —$C_2H_5$.

In another specific example, there is provided a naphthoquinone-based chalcone compound having R selected from —OH, and R1 and R2 selected from —$OCH_3$.

In another specific example, there is provided a naphthoquinone-based chalcone compound having R selected from —OH, and R1 and R2 selected from alkyl —$C_nH_2n+1$ (where n is an integer from 3-x).

In another specific example, there is provided a naphthoquinone-based chalcone compound having R selected from —OH, and R1 and R2 selected from —OH.

In another specific example, there is provided a naphthoquinone-based chalcone compound having R selected from —OH, and R1 and R2 selected from phenyl —$C_6H_5$.

In another specific example, there is provided a naphthoquinone-based chalcone compound having R selected from —OH, and R1 and R2 selected from naphthyl.

In another specific example, there is provided a naphthoquinone-based chalcone compound having R selected from —OH, and R1 and R2 selected from an amino acid.

In another specific example, there is provided a naphthoquinone-based chalcone compound having R selected from —H and R1 and R2 independently selected from —H, —$CH_3$, —$C_2H_5$, —$OCH_3$, alkyl —$C_nH_2n+1$ (where n is an integer from 3-x), —OH, phenyl —$C_6H_5$, naphthyl, or amino acid.

In another specific example, there is provided a naphthoquinone-based chalcone compound having R selected from —$CH_3$ and R1 and R2 independently selected from —H, —$CH_3$, —$C_2H_5$, —$OCH_3$, alkyl —$C_nH_2n+1$ (where n is an integer from 3-x), —OH, phenyl —$C_6H_5$, naphthyl, or amino acid.

In another specific example, there is provided a naphthoquinone-based chalcone compound having R selected from —$C_2H_5$ and R1 and R2 independently selected from —H, —$CH_3$, —$C_2H_5$, —$OCH_3$, alkyl —$C_nH_2n+1$ (where n is an integer from 3-x), —OH, phenyl —$C_6H_5$, naphthyl, or amino acid.

In another specific example, there is provided a naphthoquinone-based chalcone compound having R selected from alkyl —$C_nH_2n+1$ (where n is an integer from 3-x) and R1 and R2 independently selected from —H, —$CH_3$, —$C_2H_5$, —$OCH_3$, alkyl —$C_nH_2n+1$ (where n is an integer from 3-x), —OH, phenyl —$C_6H_5$, naphthyl, or amino acid.

In another specific example, there is provided a naphthoquinone-based chalcone compound having R selected from —OH and R1 and R2 independently selected from —H, —$CH_3$, —$C_2H_5$, —$OCH_3$, alkyl —$C_nH_2n+1$ (where n is an integer from 3-x), —OH, phenyl —$C_6H_5$, naphthyl, or amino acid.

In yet another aspect, the present disclosure provides a pharmaceutical composition that includes: a safe and effective amount of a menadione derivative as described above and a safe and effective amount of a pharmaceutically acceptable salt. In some embodiments, the methods disclosed herein include methods of treating diseases by administering such menadione derivatives and pharmaceutically acceptable salts as pharmaceutical compositions.

Compounds according to the present disclosure, such as the exemplary compounds listed above, may show an enhanced efficacy, reduced toxicity, or both in comparison to curcumin.

In order for compositions to be effective, the compounds must, preferably, be stable in a formulation, be substantially absorbable, and be biologically active at the mitochondrial target.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, "consist of" or "consist essentially of" the described features.

Definitions

As used herein, $C_1$-$C_n$ includes $C_1$-$C_2$, $C_1$-$C_3$ . . . $C_1$-$C_n$. $C_1$-$C_n$ refers to the number of carbon atoms that make up the moiety to which it designates (excluding optional substituents).

"Amino" refers to the —$NH_2$ radical.

"Cyano" refers to the —CN radical.

"Nitro" refers to the —$NO_2$ radical.

"Oxa" refers to the —O— radical.

"Oxo" refers to the =O radical.

"Thioxo" refers to the =S radical.

"Imino" refers to the =N—H radical.

"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). Unless stated otherwise specifically in the specification, an alkyl group is optionally substituted by one or more of the following substituents: halo, cyano, nitro, oxo, thioxo, imino, oximo, trimethylsilanyl, —ORa, —SRa, —OC(O)—Rf, —N(Ra)2, —C(O)Ra, —C(O)ORa, —C(O)N(Ra)2, —N(Ra)C(O)ORf, —OC(O)—NRaRf, —N(Ra)C(O)Rf, —N(Ra)S(O)tRf (where t is 1 or 2), —S(O)tORa (where t is 1 or 2), —S(O)tRf (where t is 1 or 2) and —S(O)tN(Ra)2 (where t is 1 or 2) where each Ra is independently hydrogen, alkyl, haloalkyl, cycloalkyl, aryl, aralkyl, heterocycloalkyl, heteroaryl, or heteroarylalkyl, and each Rf is independently alkyl, haloalkyl, cycloalkyl, aryl, aralkyl, heterocycloalkyl, heteroaryl, or heteroarylalkyl "Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. Unless stated otherwise specifically in the specification, an alkenyl group is optionally substituted by one or more of the following substituents: halo, cyano, nitro, oxo, thioxo, imino, oximo, trimethylsilanyl, —ORa, —SRa, —OC(O)—Rf, —N(Ra)2, —C(O)Ra, —C(O)ORa, —C(O)N(Ra)2, —N(Ra)C(O)ORf, —OC(O)—NRaRf, —N(Ra)C(O)Rf, —N(Ra)S(O)tRf (where t is 1 or 2), —S(O)tORa (where t is 1 or 2), —S(O)tRf (where t is 1 or 2) and —S(O)tN(Ra)2 (where t is 1 or 2) where each Ra is independently hydrogen, alkyl, haloalkyl, cycloalkyl, aryl, aralkyl, heterocycloalkyl, heteroaryl, or heteroarylalkyl, and each Rf is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. Unless stated otherwise specifically in the specification, an alkynyl group is optionally substituted by one or more of the following substituents: halo, cyano, nitro, oxo, thioxo, imino, oximo, trimethylsilanyl, —ORa, —SRa, —OC(O)—Rf, —N(Ra)2, —C(O)Ra, —C(O)ORa, —C(O)N(Ra)2, —N(Ra)C(O)ORf, —OC(O)—NRaRf, —N(Ra)C(O)Rf, —N(Ra)S(O)tRf (where t is 1 or 2), —S(O)tORa (where t is 1 or 2), —S(O)tRf (where t is 1 or 2), and —S(O)tN(Ra)2 (where t is 1 or 2) where each Ra is independently hydrogen, alkyl, haloalkyl, cycloalkyl, aryl, aralkyl, heterocycloalkyl, heteroaryl, or heteroarylalkyl, and each Rf is independently alkyl, haloalkyl, cycloalkyl, aryl, aralkyl, heterocycloalkyl, heteroaryl, or heteroarylalkyl.

"Aminoalkyl" refers to a radical of the formula -Rc-N(Ra)2 or -Rc-N(Ra)-Rc, where each Rc is independently an alkylene chain as defined above, for example, methylene, ethylene, and the like; and each Ra is independently hydrogen, alkyl, fluoroalkyl, cycloalkyl, aryl, aralkyl, heterocycloalkyl, or heteroaryl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) p-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —Rb—ORa, —Rb—OC(O)—Ra, —Rb—OC(O)—ORa, —Rb—OC(O)—N(Ra)2, —Rb—N(Ra)2, —Rb—C(O)Ra, —Rb—C(O)ORa, —Rb—C(O)N(Ra)2, —Rb—O-Rc-C(O)N(Ra)2, —Rb—N(Ra)C(O)ORa, —Rb—N(Ra)C(O)Ra, —Rb—N(Ra)S(O)tRa (where t is 1 or 2), —Rb—S(O)tORa (where t is 1 or 2), —Rb—S(O)tRa (where t is 1 or 2), and —Rb—S(O)tN(Ra)2 (where t is 1 or 2), where each Ra is independently hydrogen, alkyl, haloalkyl, cycloalkyl, cycloalkylalkyl, aryl, aralkyl, heterocycloalkyl, heteroaryl, or heteroarylalkyl, each Rb is independently a direct bond or a straight or branched alkylene or alkenylene chain, and Rc is a straight or branched alkylene or alkenylene chain.

"Aryloxy" refers to a radical bonded through an oxygen atom of the formula-O-aryl, where aryl is as defined above.

"Aralkyl" refers to a radical of the formula -Rc-aryl where Rc is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula -Rd-aryl where Rd is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula -Re-aryl, where Re is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms.

"Halo" or "halogen" refers to bromo, chloro, fluoro or iodo substituents.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heteroalkyl" refers to a straight or branched hydrocarbon chain alkyl radical containing no unsaturation, having from one to fifteen carbon atoms (e.g., C1-C15 alkyl) consisting of carbon and hydrogen atoms and one or two heteroatoms selected from O, N, and S, wherein the nitrogen or sulfur atoms may be optionally oxidized and the nitrogen atom may be quaternized.

In some embodiments, the compounds disclosed herein contain one or more asymmetric centers and thus give rise to enantiomers, diastereomers, and other stereoisomeric forms that are defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH.

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M, et al., "Pharmaceutical Salts," Journal of Pharmaceutical Science, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,Ndibenzylethylenediamine, chloroprocaine, hydrabamine, choline, betaine, ethylenediamine, ethylenedianiline, N methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

In some embodiments, the compounds described herein exist in prodrug form. Also described herein are methods of treating diseases by administering such prodrugs. Further described herein are methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds described herein. The amino acid residues include but are not limited to the 20 naturally occurring amino acids and also includes 4-hydroxyproline, hydroxylysine, demosineisodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls.

In certain embodiments, the compounds of Formula I described herein are administered as a pure chemical. In other embodiments, the compounds of Formula I described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice. One embodiment provides a pharmaceutical composition comprising a pharmaceutically acceptable carrier and a compound of Formula (I), or a pharmaceutically acceptable salt thereof.

In certain embodiments, the compound of Formula (I) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These compositions described herein include those suitable for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid, or liquid form, which includes one or more of a disclosed compound, as an active ingredient, in a mixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof.

When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (optionally, cottonseed, groundnut, corn, germ, olive, castor and sesame oils), glycerol, tetrahydrofuryl alcohol, polyethylene glycols and fatty acid esters of sorbitan, cyclodextrins, and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable nonirritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches, and inhalants. In some embodiments, the active component is mixed under sterile conditions with a pharmaceutically acceptable carrier, and with any preservatives, buffers, or propellants as required.

In some embodiments, the ointments, pastes, creams, and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation, or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, and amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof.

Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5, and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylatechlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

The following examples describe some exemplary modes of making and practicing certain compositions and methods that are described herein. It should be understood that these examples are for illustrative purposes only and are not meant to limit the scope of the compositions and methods described herein.

EXAMPLES

Exemplary Synthetic Procedure for R-Substituted Naphthoquinone-Based Chalcone Derivatives

Step 1; Menadione Converted to 2-Methylnaphthalene-1,4-Diol (Menadiol-RLS2)

To a solution of sodium hydrosulfite (15.2 g, 0.087 mol) in deionized water (40 mL) was added a solution of menadione (5 g, 0.029 mol) in EtOAc (60 mL) at room temperature. After being stirred at room temperature for 60 minutes, the reaction mixture was poured into a separatory funnel and extracted twice with EtOAc. The combined organic layers were dried with $MgSO_4$ and filtered. The filtrate was concentrated in vacuo, and the resulting light purple solid was confirmed with NMR and MS to be Menadiol (4.92 g, 0.028 mol, 98%) as a light purple solid;

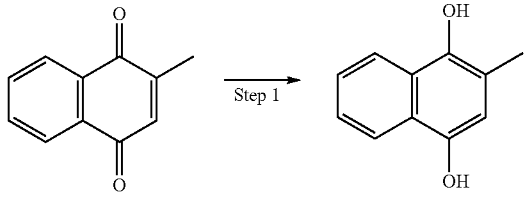

RLS2

Step 2; Methylation of 2-Methylnaphthalene-1,4-Diol to 1,4-Dimethoxy-2-Methylnaphthalene (Methyl Protected Menadiol-RLS3)

To a solution of Menadiol (0.5 g, 2.87 mmol) in DMF (10 mL) heated to 90° C. was added potassium carbonate (2.56 g, 18.5 mmol). After being stirred at 90° C. for 2 minutes, methyl iodide (1.4 mL, 11.5 mmol) was added to the Menadiol solution. Heat was maintained at 90° C. for 30 minutes and confirmed absence of starting material with TLC. The mixture was added to a separatory funnel with 1M HCl and then extracted with EtOAc. The combined organic layers were dried with $MgSO_4$ and filtered. The filtrate was concentrated in vacuo, and the resulting residue was purified by flash column chromatography on silica gel (eluted with EtOAc/Hexane=1:20) to afford Methyl Protected Menadiol (429 mg, 2.1 mmol, 74%) as a red oil. The product was confirmed on NMR and MS and carried forward.

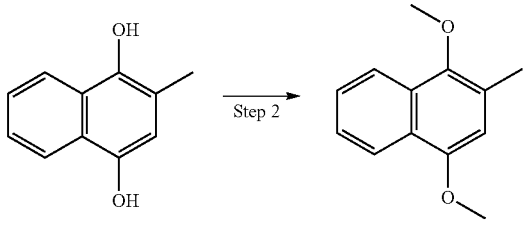

RLS3

Step 3; 1,4-Dimethoxy-3-Methyl-2-Naphthaldehyde-RLS4

To a solution of Methyl Protected Menadiol (200 mg, 1.00 mmol) in dry DCM (2 mL) was set to cool and stirred to −45° C. After being stirred for 15 minutes, silver trifluoromethanesulfonate (768 mg, 3.00 mmol) was added under argon. After being stirred at −45° C. for 10 minutes, dichloromethyl methyl ether (345 mg, 3.00 mmol) was added dropwise. After 10 minutes, the mixture was checked by TLC and the temperature warmed to 0° C. The mixture was stirred for 10 minutes at 0° C., then TLC confirmed starting material was gone and water was added to neutralize and stirred at room temperature for 10 minutes. This mixture was then poured into a separatory funnel and extracted twice with EtOAc. The combined organic layers were washed with brine then dried with $MgSO_4$ and filtered. The filtrate was concentrated in vacuo, and the resulting residue was washed on silica gel with EtOAc and filtered. The residue was again concentrated and washed with hexane 3 times and the hexane layers concentrated. The product was confirmed on NMR and MS and carried forward. (124.4 mg, 0.54 mmol, 54%) as a brown solid;

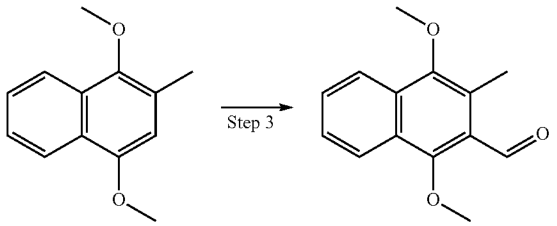

RLS4

Step 4; (1E,4Z,6E)-1,7-Bis(1,4-Dimethoxy-3-methylnaphthalen-2-yl)-5-Hydroxyhepta-1,4,6-trien-3-one (Dimer-RLS5)

To a solution of 2, 4 pentanedione (49 mg, 0.49 mmol) and boric acid (30 mg, 0.49 mmol) in EtOAc (10 mL) was heated to 40° C. for 1 hr. Tributyl borate (225 mg, 0.98 mmol) was added then added the methyl protected aldehyde (239 mg, 0.98 mmol) and heated at 40° C. for 2 hr. Added N-butyl amine (53.6 mg, 0.73 mmol) then heated mixture at 40 C for 24 hrs. 10% HCl (10 mL) was added and heated to 60° C. for one hour before allowing to cool and then added mixture to separatory funnel and extracted 2 times with EtOAc. The organic layers were combined then washed with brine and dried with $MgSO_4$. The filtrate was concentrated in vacuo, and the resulting residue washed with hexane and the product was checked by TLC to afford Methyl Protected Bis-Methyl Naphthoquinone Heptadione Chalcone (Methyl protected BMN4QHDC-RLS5) (115 mg, 0.22 mmol, 45%) as a yellow solid.

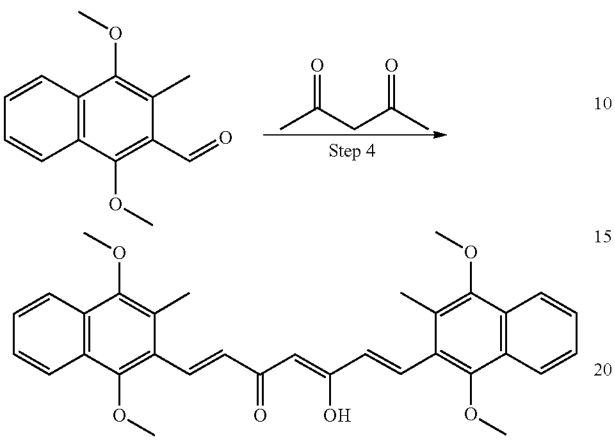

RLS5

Step 5; Demethoxylation of Dimer (3,3'-((1E,3Z, 6E)-3-Hydroxy-5-Oxohepta-1,3,6-triene-1,7-diyl)Bis (2-Methylnaphthalene-1,4-dione)-RLS6 Enol To a solution of Methyl Protected BMN4QHDC (52 mg, 0.01 mmol) in 1:1 $MeCN/H_2O$ (2 mL) was added ceric ammonium nitrate (215 mg, 0.04 mmol) at room temperature. After being stirred at room temperature for 30 minutes, the reaction mixture was poured into 1M HCl. This mixture was extracted twice in a separatory funnel with EtOAc. The combined organic layers were dried with $MgSO_4$ and filtered. The filtrate was concentrated in vacuo, and the resulting residue was purified by flash column chromatography on silica gel (eluted with $MeOH/CH_2Cl_2$=1:20) to afford BMN4QHDC or RLS6 Enol (26.7 mg, 0.006 mmol, 58%) as a red solid.

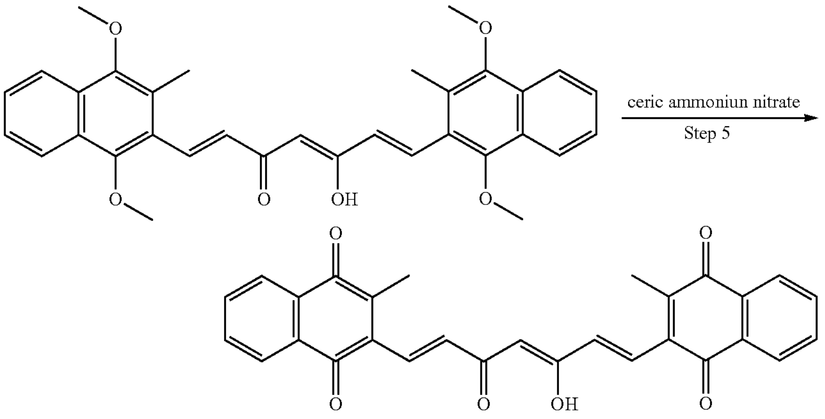

RLS6 Enol

All chemical reagents were obtained from commercial suppliers as reagent or HPLC grade and used without further purification in the making of an R-substituted naphthoquinone-based chalcone compound. The following chemical formula depicts the final product known as RLS6.

RLS6

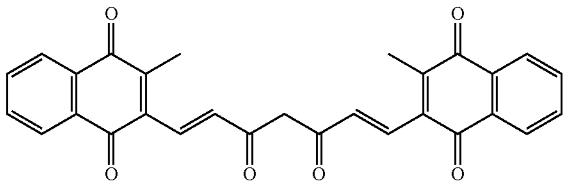

Chemical Formula: $C_{29}H_{20}O_6$
Exact Mass: 464.1260
Molecular Weight: 464.4730
m/z: 464.1260 (100.0%), 465.1293 (31.4%), 466.1327 (4.7%), 466.1302 (1.2%)
Elemental Analysis: C, 74.99; H, 4.34; O, 20.67

$^1H$ and $^{13}C$ NMR

The NMR data were obtained on a 500 MHZ FT-NMR model ECA-500 JEOL (Peabody, MA, USA). Coupling constants (J values) are recorded in hertz (Hz). 20 mg of compound were dissolved in Chloroform D ($CDCl_3$) in a 5 mm NMR tube for both $^1H$ and $^{13}C$ spectrum.

Mass Spectrometry

Mass spectra of compounds were obtained via direct injection on a Waters Synapt HDMS QToF with Ion Mobility. Briefly, a 1 mg/mL solution of compound in acetonitrile was directly injected into the ESI-MS at a flow rate of 30 μL/min. The Mass Spectrometer was set to scan from 100-2000 amu in 0.5 second intervals in positive mode for 30 seconds. Mass spectra were extracted and combined from the TIC chromatogram. For high resolution mass spectrometry, the instrument was first calibrated using a positive mode sodium iodide method per manufacturer protocols.

Cellular Metabolic Activity

Autobioluminescent Human Epithelial Kidney cells (HEK-293, 490 Biotech) and Human Liver cells (Hep-G2, 490 Biotech) and Human primary astrocytes (490 Biotech) were seeded at 10,000 kidney cells/well, or 50,000 liver cells/well, in 96-well tissue culture treated plates (Falcon) in growth media. The growth media consists of the following: DMEM (Hyclone), 10% heat-inactivated FBS (Gibco), 1% Sodium Pyruvate (HyClone), 1% antibiotic/antimyotic (Hyclone) and 100 μg G418/ml (Gibco). Cells were grown for 2 days prior to treatment with dimenadione derivative compounds. The media was aspirated and cells were washed with 1×PBS (Fisher, SH30256.01) and treated with serial dilutions ranging from 5 fM to 5 μM (1 mL/well) dimenadione derivative compounds. The treated cells were incubated at 37° C. and 5% $CO_2$ for x hours. At each concentration, bioluminescence was measured with either a BMG Labtech clarioSTAR plate reader or an IVIS CCD camera system. Any changes in cell bioluminescence were recorded as photons/per well. The replicates were averaged, and all conditions were normalized to background light detection (medium-only control wells). The vehicle-only controls were compared to the untreated controls to make sure there was not change in metabolic activity due to the solvent. All other treatments were then compared to the vehicle control. The relative change in light output was measured between each treatment and the vehicle control at each timepoint. The amount of light being made is proportional to metabolic activity (as measured by FMNH2 availability, which provides the same information as a traditional ATP content assay (i.e., CellTiter Glo).

StemoniX (Organ-Specific In Vitro Assays)

Pre-clinical plates containing biologically relevant human microOrgans® will be used to test organ-specific efficacy of the compounds. Engineered from human induced pluripotent stem cells (iPSC), these microOrgan® platforms enable high throughput human drug screening without the need for drugs to enter a human body. The compounds will be tested in neuronal microOrgans to determine the effect of the molecule on neuronal cell function and viability, as revealed by responses to neurotransmitters, neurotransmitter receptor expression, spontaneous and synchronous neuronal cell firing, and high-density functional synapses resulting in active neuronal circuitry. Test compounds (quinone-containing compounds) and purterbagens (organophosphates) identified to impair normal functioning of the human microOrgans® will either be dissolved in DMSO or in powder format, if dissolved in DMSO, the test compounds will be provided at a 1000× of the highest concentration needed in the assay plates. The stock for each test compound will be placed into a 96-well or 384-well plate. The test compounds will be tested in both microBrain® 3D and microHeart® 3D assay-ready plates. Each plate will be analyzed for impact on the calcium oscillations as well as the ATP-levels. Functional assessment of test compounds impact on calcium oscillations will be measured by a calcium flux assay. This is to determine the impact of the test compounds on the spontaneous and synchronous calcium-oscillations of the microBrain® 3D neural-spheroid cultures, as well as the microHeart® 3D cardio-spheroid cultures, using the FLIPR Tetra® high-throughput cellular screening system (Molecular Devices). The following protocol will be used for FLIPR screening: The day before screening, the media will be replaced with phenol red-free media to improve the signal-to-noise in FLIPR assay. Full plate images will be captured in brightfield using the CellDiscoverer 7-quality check for assessment of spheroid size and shape. Diluted test compounds, ATP modulator, and DMSO vehicle control will be added to assay-ready plates and will be Incubated for 24 hours. Calcium dye (C6) will be added to each well in microBrain® 3D plate and incubated at 37° C./5% $CO_2$ for 2 hours. Test compounds and controls (4-aminopyridine, muscimol) will be added and calcium oscillations measured for 10 minutes at 2 Hz at each timepoint: 0 minutes (just following addition of test compounds), 30 minutes, 60 minutes, 120 minutes, and 240 minutes. Calcium dye (C6) will be added to each well in microHeart® 3D plate and incubated at 37° C./5% $CO_2$ for 2 hours. Test compounds and controls (nifedipine, lidocaine) will be added and calcium oscillations measured for 90-120 seconds at 10 Hz at each timepoint: 0 minutes (just following addition of compounds), 30 minutes, 60 minutes, 120 minutes, and 240 minutes. Analysis of FLIPR data from neural-spheroid cultures will be against seven parameters: i. Peak Count; ii. Average Peak Amplitude; iii. Peak Amplitude Standard Deviation; iv. Average Peak Spacing; v. Average Peak Rise Time; vi. Average Peak Decay Time; and vii. Average Peak Width at 10% Amplitude. Analysis of FLIPR data from cardio-spheroid culture will be against five parameters: i. Beat Rate; ii. Average Peak Amplitude; iii. Peak Rise Time; iv. Peak Decay Time; and v. Peak Width at 10% Amplitude. Assessment of impact on (energy) metabolism and impact on ATP-Levels will be measured by the CellTiter-Glo® (CTG) Reagent. The goal is to determine the impact of the test compounds (quinone-containing compounds and organophosphates) on the (energy) metabolism (i.e., ATP levels), of the microBrain® 3D neural-spheroid cultures, as well as the microheart 3D cardio-spheroid cultures, using the luminescent CTG reagent for 3D cultures (Promega). The following protocol will be used for assessing cytotoxicity: after the calcium flux assay is performed, an 8× wash out with fresh phenol red-free media will be completed and test compounds will be added (per time-points, as above). Media will be removed and after 30 minutes CTG reagent added for 25 minutes. Plate will be read on a plate reader to collect luminescence data (data will include all time points).

BioSymetrics (in vivo assays)

Using a zebrafish platform to directly examine the impact of the compounds in vivo, while also examining their effect on ATP Synthase inhibitors. Larval zebrafish, owing to their transparency, evolutionary similarity to higher vertebrates, permeability to small molecules, and rapid growth, are a scalable, attractive model for phenotypic screening. Since phenotypes observed during zebrafish development can have immediate relevance to processes in higher vertebrates, drugs identified in phenotype-driven screens often have corresponding effects in mammalian systems. This will provide several lines of evidence on the small molecule, including: a) Identification of in vivo toxicity in a vertebrate model organism; b) Impact on the consequences of reduced ATP production via ATP Synthase inhibition; and c) Dose-related effects on mitochondrial respiration in vivo.

Zebrafish (AB strain) will be obtained from the Zebrafish International Resource Center, and maintained and crossed according to standard methods. Fertilized eggs will be collected and placed in egg water (60 mg/L Instant Ocean salts (Spectrum Brands, Madison, WI) in ddH2O), and positioned in an incubator set at 28.5° C. with a 14/10 hr light/dark cycle. Embryos will be staged as previously described. Embryos will be collected at 3 hpf, 7 hpf, 12 hpf, 24 hpf, 30 hpf, and 48 hpf for experimentation. These time-points fall within the blastula (3 hpf), gastrula (7 hpf), segmentation (12 hpf), segmentation/pharyngula transition (24 hpf), mid-pharyngula (30 hpf), and hatching (48 hpf) periods in zebrafish embryonic development.

Oligomycin, FCCP, and sodium azide will be obtained from Sigma-Aldrich (St. Louis, MO). Titrations of each agent will be performed at each time-point post-fertilization, to determine the concentration that produced the maximum change in respiration without inducing death within the experimental timeframe. Concentrated stocks of oligomycin and FCCP will be prepared in DMSO at 10 mM and 20 mM, respectively. A concentrated stock of sodium azide (5 M) will be prepared in phosphate buffered saline.

Overall cellular respiration (OCR) measurements will be performed using the XF24 Extracellular Flux Analyzer (Seahorse Bioscience, Billerica, MA). Dual-analyte sensor cartridges will be soaked in XF Calibrant Solution (Seahorse Bioscience, Billerica, MA) in 24 well cell culture microplates (Seahorse Bioscience, Billerica, MA) overnight at 28.5° C., to hydrate. Approximately one hour prior to experimentation, the injection ports on the sensor cartridge will be filled with 100 μl of the appropriate treatments, which will then be loaded into the XF24 instrument for calibration. Embryos will be staged and placed into 20 of 24 wells on an islet microplate. Islet plate capture screens will be placed over the top of the measurement area to keep the embryos in place. Four wells will serve as temperature control wells on each plate (A1, B3, C4 and D6). Preliminary experiments will be performed to determine the number of embryos needed to achieve OCRs that fall within the recommended specifications of the XF24 instrument. Each well will be filled with 700 μL of egg water. Plates will be incubated in a non-$CO^2$ incubator at 28.5° C. until the completion of sensor cartridge calibration. After calibration the sensor microplate will be replaced with the prepared islet plate. One measurement cycle will consist of a brief wait period to acclimate the plate. 2 min mix, 1 min wait, and 1.5 min measurement. Six measurement cycles will be taken to establish basal rates, which will then be followed by treatment injections and 18 additional measurement cycles. OCRs will be calculated using a modified AKOS algorithm that takes into account oxygen diffusion through the plate and atmospheric leak, in addition to the oxygen consumed by the organism. OCR measurements will be taken at cycles five and six, which will then be averaged. This average value is the total basal respiration. Treatment rates will be taken at two consecutive measurement cycles at the maximum OCR (after FCCP treatment) or the minimum OCR (after oligomycin or sodium azide treatment), which will then be averaged. This average value is the treatment OCR.

Similarly, for extracellular acidification rate (ECAR) measurements, the fifth and sixth measurements will be averaged to provide the basal ECAR, and the cycles at which the maximal or minimal OCRs are taken will be used for the treatment ECAR averages.

Buffer capacity will be calculated by monitoring the change in pH of the running media with 5 additions of a known quantity of protons from the addition of 0.1 N HCl. The experimentally determined ECAR will be converted to PPR by dividing ECAR by the buffer capacity. Respiration and media acidification rate measurements for embryos at each developmental stage will be analyzed and normalized per embryo, as the mass of the embryo and the protein content of each embryo does not change significantly during development up to the hatching period.

Analysis of lactate production will be performed on embryos placed into individual wells of a 24 well assay plate at a density of 5 embryos per mL. Each well will contain 2 mL of 0.2 μm filtered egg water. Embryos will then be incubated for 1.5 hr, and 1 mL media will be sampled from each well. Samples will be taken in triplicate for each of the 7 time-points (3, 7, 12, 24, 30, 48 hpf). Control and treatment (sodium azide) groups will be set up and run simultaneously. Sodium azide concentrations will be used to correspond with the concentrations used for embryos in XF24 experiments. After sodium azide is added to embryos at each time-point, embryos will be incubated according to the approximate XF assay time before the media is taken for sampling. Samples of egg water will be taken in 1 ml aliquots and stored at −80° C. until needed. Lactate assays will be performed on all samples according to standard methods.

Western analysis of COX IV protein levels will be performed on triplicate samples containing thirty embryos taken at each time-point post-fertilization, and stored at −80° C. until needed. For protein extraction, microfuge tubes containing thirty embryos will be thawed on ice, and 150 μL cold RIPA buffer (150 mM NaCl, 1 mM EDTA, 50 mM Tris HCl PH 7.5, 1% NP-40) containing 1:100 protease inhibitor cocktail (Sigma P8340) will be added. Embryos will be gently homogenized with a microfuge pestle. Tubes will be rotated for 10 min at 4° C., then spun at 12,000 g at 4° C. for 10 min. The supernatant will be transferred to a new tube, and the protein concentration will be determined by BCA protein assay. In each well of a 4-20% Tris-glycine polyacrylamide gel (Pierce), 30 μg of protein will be loaded per time-point. After electrophoresis, proteins will be transferred onto an Immobilon-P membrane (Millipore) overnight at 25 V. Western blot analysis will follow established methods, with the following modifications. Membranes will be blocked with 5% milk in TN (50 mM Tris-HCl, pH7.5, and 0.15 M NaCl), then probed using 1/1000 beta actin antibody (Sigma A2228) or 1/1000 COX IV antibody (Abcam 16056) in TN for 2 hr. Membranes will be washed three times in TN, 10 min per wash. To the membrane probed with beta actin, 1/1000 goat anti-mouse HRP in 5% milk/TN will be added for 2 hr. To the membrane probed with COX IV, 1/3000 goat anti-rabbit IgG HRP in TN will be added for 2 hr. Membranes will be washed three times in TNT (0.1% Triton X-100, 50 mM Tris-HCl, pH 7.5, and 0.5 M NaCl), 10 min per wash, then with TN three times, 10 min per wash. Novex HRP Chromogenic Substrate (Invitrogen WP20004) will be added to the membrane to visualize bands. Membranes will then be rinsed in ddH2O and dried. Blots will be scanned and bands quantified using ImageJ software (NIH). COX IV densitometry values will be normalized to beta actin (loading control) values, with the value at 3 hpf set to 1. Respiration rates at each time-point will be normalized to these values. Each experiment will be repeated 7-8 times with different clutches. Statistical analyses will be performed using Kaleidagraph v4.0 (Synergy Software), either one-way ANOVA followed by Student-Newman-Keuls post hoc test for multiple comparisons or Student's t-test for single comparisons. Differences will be considered statistically significant when $p<0.05$.

Example 1 Synthesis of R-Substituted Naphthoquinone-Based Chalcone Derivative Steps 1-5 in FIG. 1 describe an exemplary synthesis that was performed to give an R-substituted naphthoquinone-based chalcone compound.

Figure 2A:
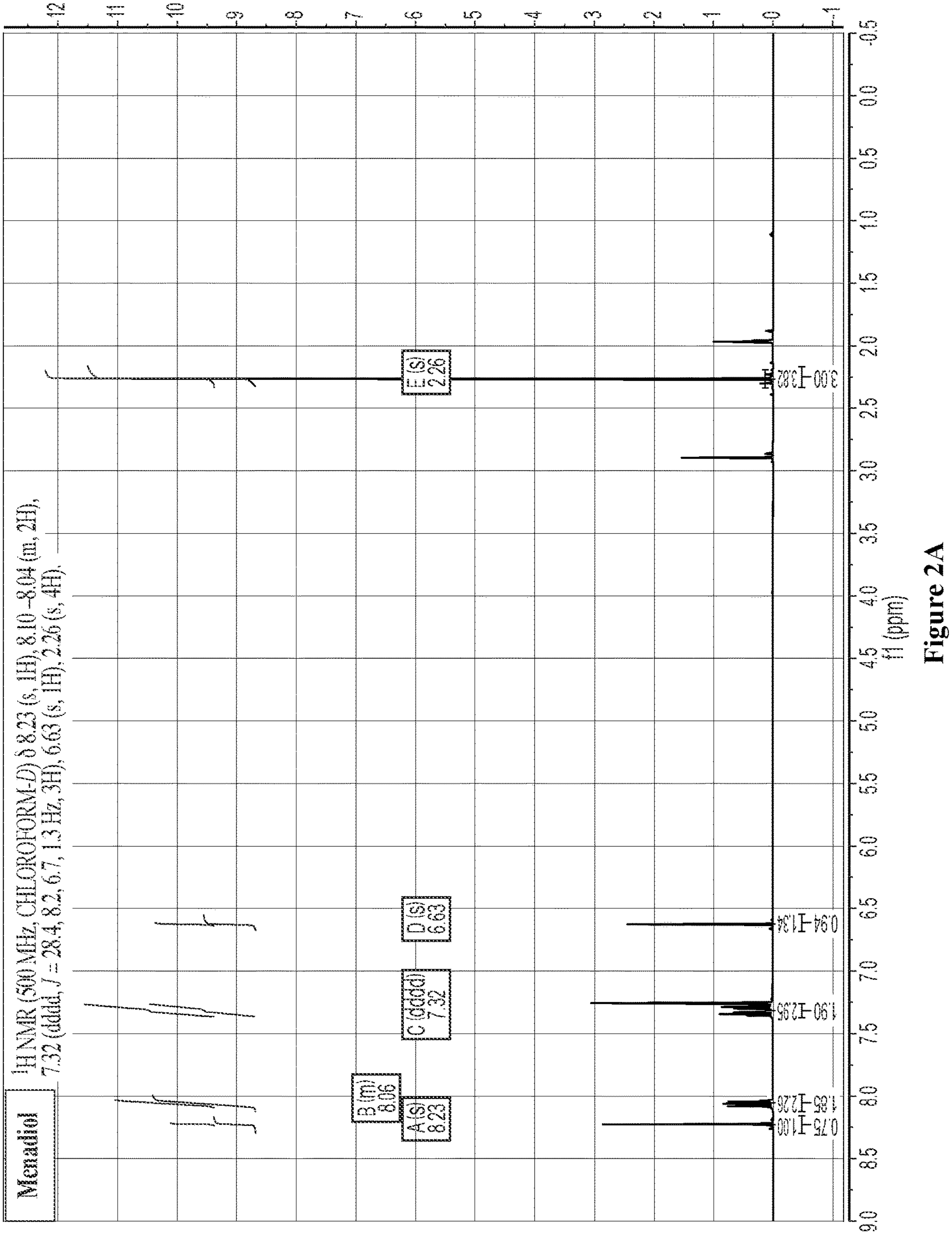
FIG. 2A is a graph that shows the $^1$H NMR for an intermediate (2-methylnaphthalene-1,4-diol) of an exemplary compound of formula 1.
Figure 2B:
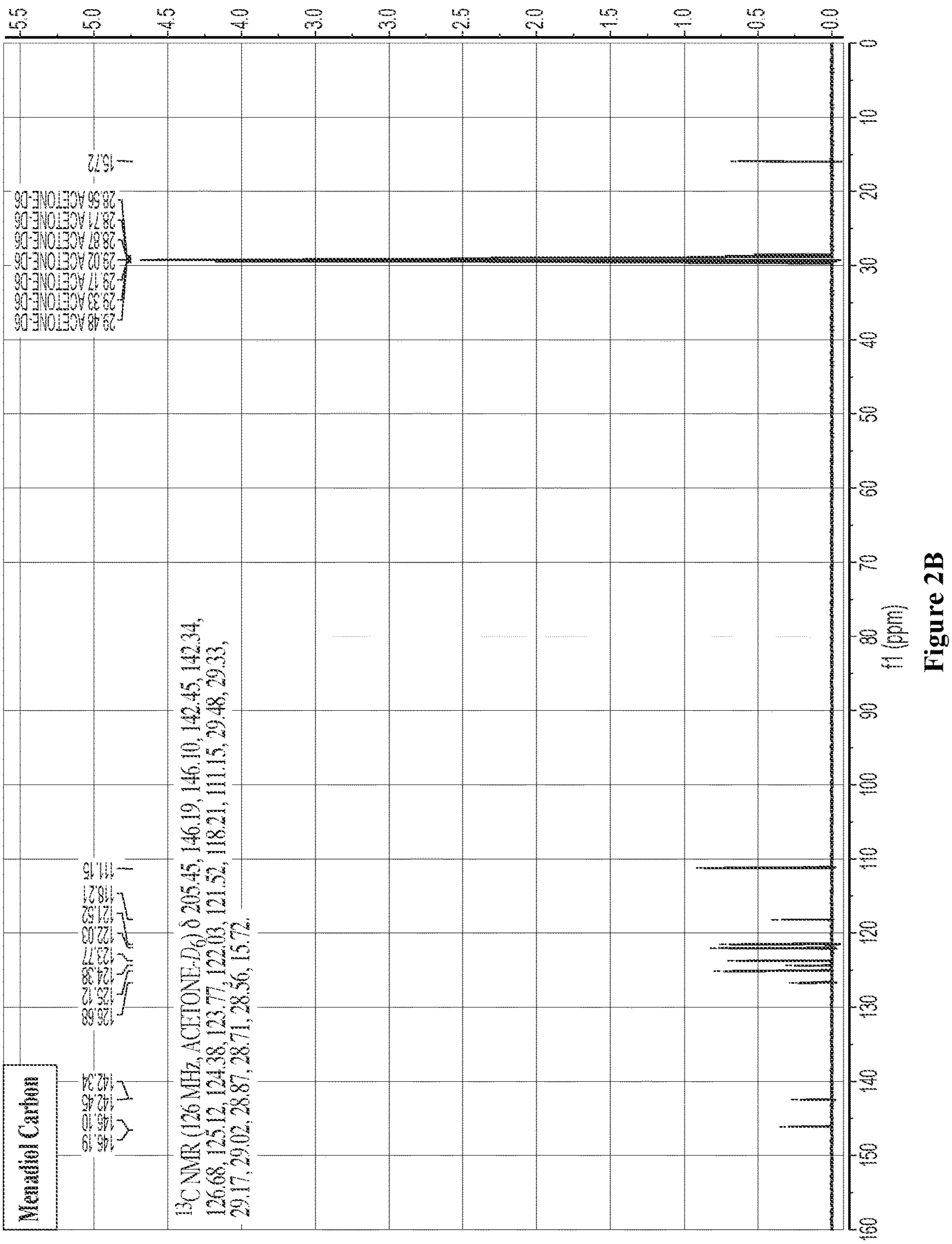
FIG. 2B is a graph that shows the $^{13}$C NMR for an intermediate (2-methylnaphthalene-1,4-diol) of an exemplary compound of formula 1.
Figure 2C:
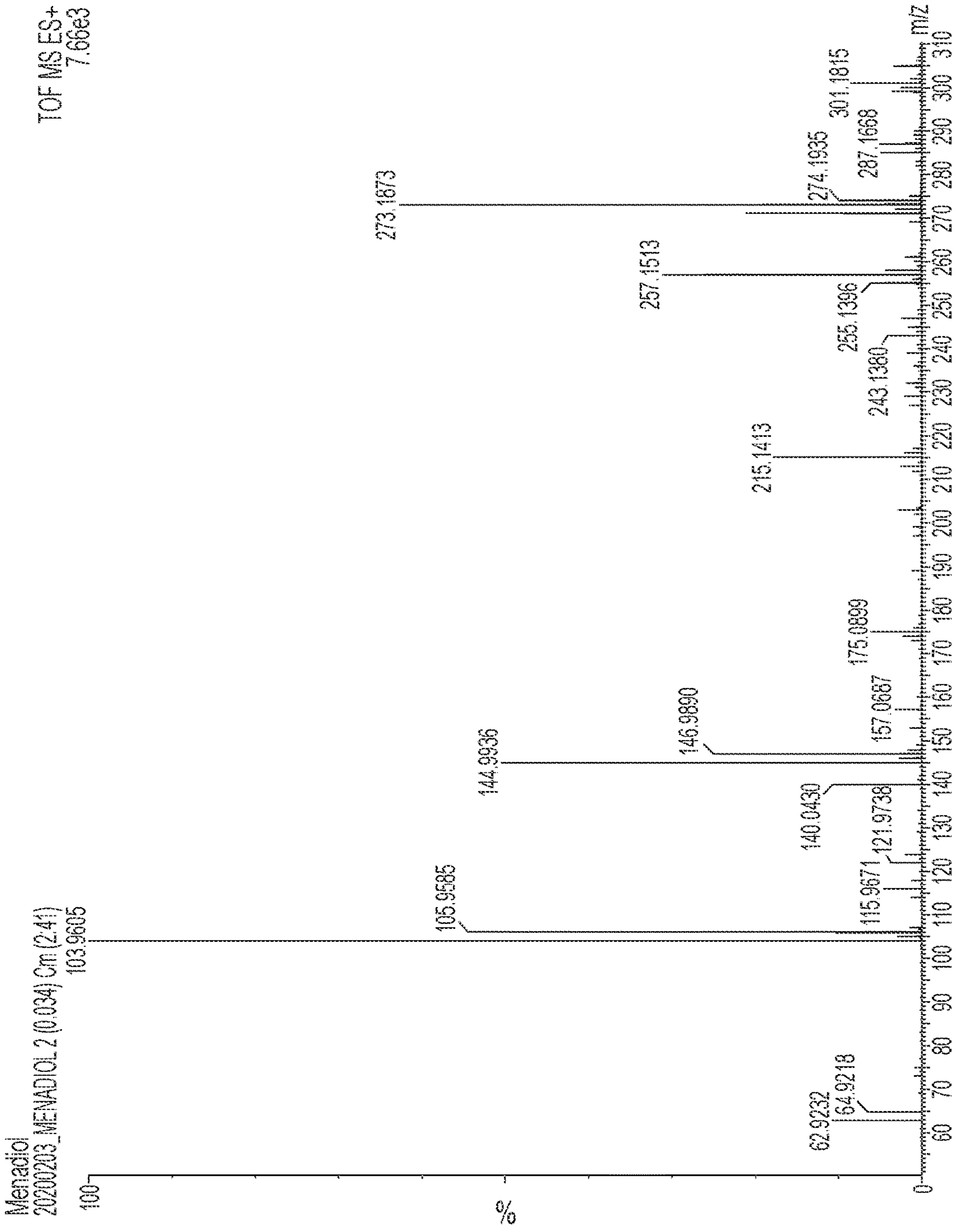
FIG. 2C is a graph that shows the Mass Spectrometry for an intermediate (2-methylnaphthalene-1,4-diol) of an exemplary compound of formula 1.

$^{1}H$ NMR spectrum of the intermediate compound RLS2 resulting from Step 1 (500 MHZ, Choloform-D) is shown in FIG. 2A; $^{1}H$ NMR δ 8.23 (s, 1H), 8.10-8.04 (m, 2H), 7.32 (ddd, J=28.4, 8.2, 6.7, 1.3 Hz, 3H), 6.63 (s, 1H), 2.26 (s, 3H). $^{13}C$ NMR spectrum of the intermediate compound RLS2 resulting from Step 1 (126 MHz, Chloroform-D) is shown in FIG. 2B; $^{13}C$ NMR δ 205.45, 146.19, 146.10, 142.45, 142.34, 126.68, 125.12, 124.38, 123.77, 122.03, 121.52, 118.21, 111.15, 29.48, 29.33, 29.17, 29.02, 28.87, 28.71, 28.56, 15.72. Mass spectroscopy of the intermediate compound RLS2 resulting from step 1 is shown in FIG. 2C; MS (ESI) calculated for $C_{11}H_{11}O_2$ (M+H) 175.0759, found 175.0899.

Figure 3A:
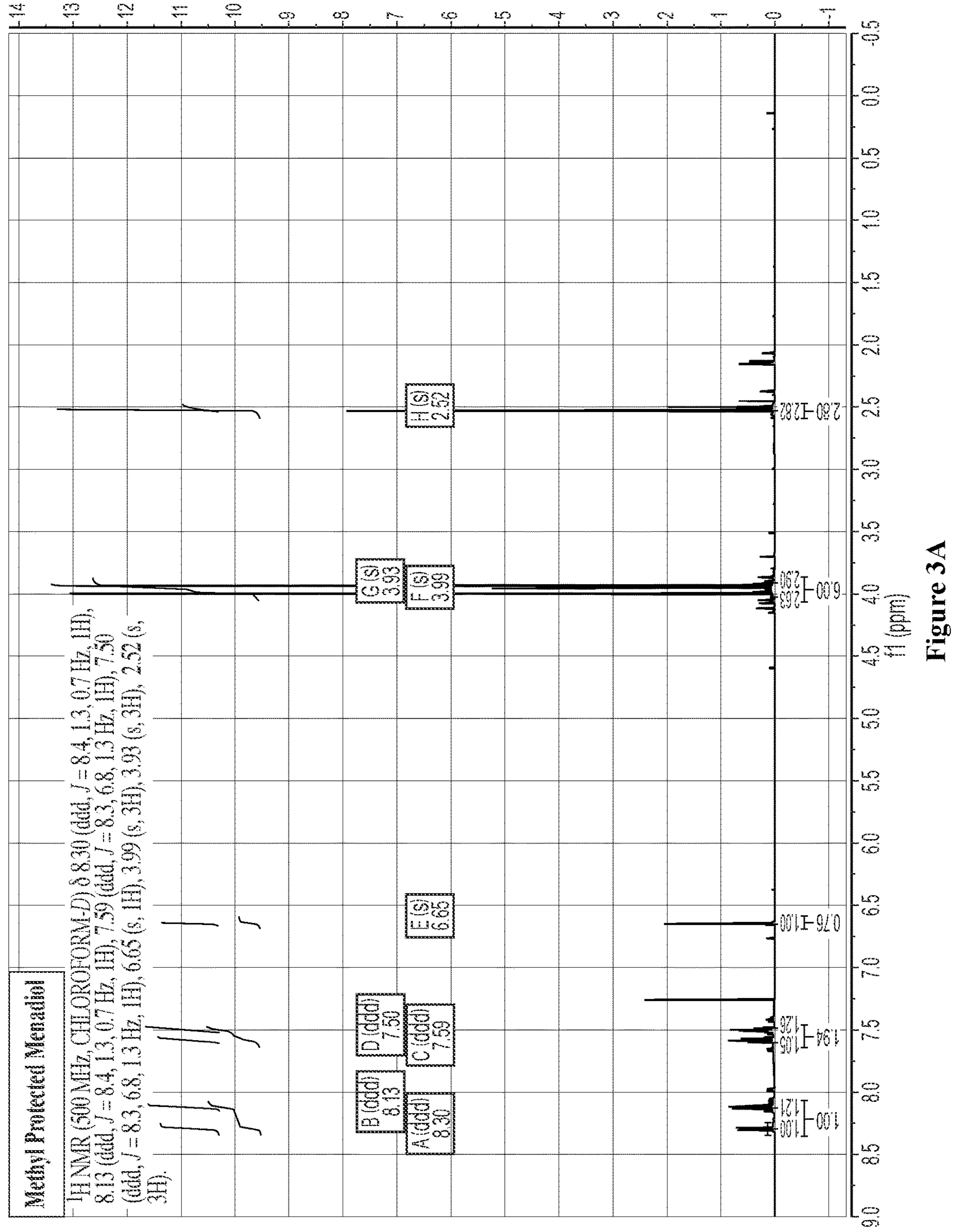
FIG. 3A is a graph that shows the $^1$H NMR for an intermediate (1,4-Dimethoxy-2-Methylnaphthalene) of an exemplary compound of formula 1.
Figure 3B:
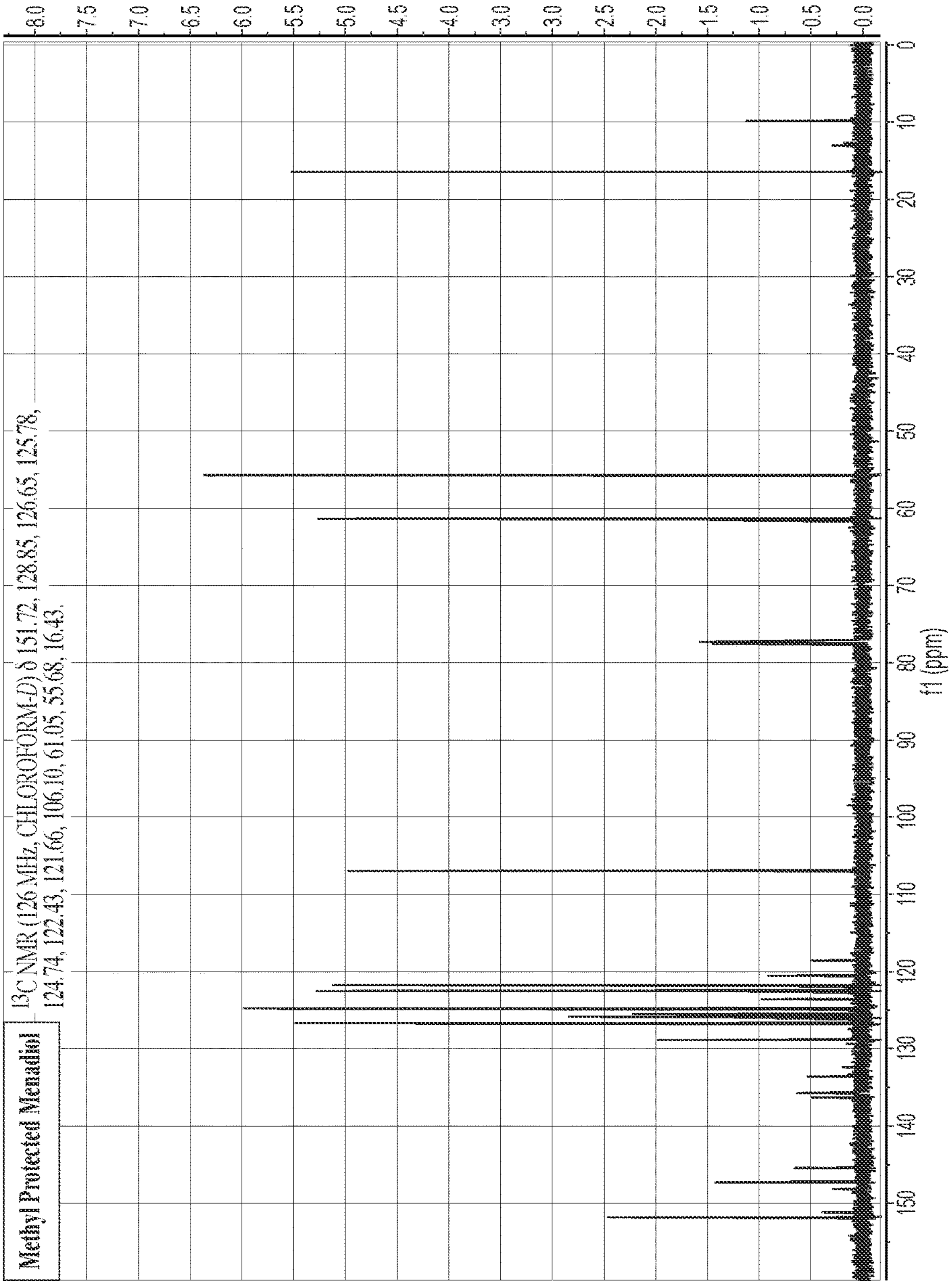
FIG. 3B is a graph that shows the $^{13}$C NMR for an intermediate (1,4-Dimethoxy-2-Methylnaphthalene) of an exemplary compound of formula 1.
Figure 3C:
FIG. 3C is a graph that shows the Mass Spectrometry for an intermediate (1,4-Dimethoxy-2-Methylnaphthalene) of an exemplary compound of formula 1.

$^1$H NMR spectrum of the intermediate compound RLS3 resulting from Step 2 (500 MHz, Chloroform-D) is shown in FIG. 3A; $^1$H NMR δ 8.30 (ddd, J=8.4, 1.3, 0.7 Hz, 1H), 8.13 (ddd, J=8.4, 1.3, 0.7 Hz, 1H), 7.59 (ddd, J=8.3, 6.8, 1.3 Hz, 1H), 7.50 (ddd, J=8.3, 6.8, 1.3 Hz, 1H), 6.65 (s, 1H), 3.99 (s, 3H), 3.93 (s, 3H), 2.52 (s, 3H). $^{13}$C NMR spectrum of the intermediate compound RLS3 resulting from Step 2 (126 MHZ, Chloroform-D) is shown in FIG. 3B; $^{13}$C NMR δ 151.72, 128.85, 126.65, 125.78, 124.74, 122.43, 121.66, 106.10, 61.05, 55.68, 16.43. Mass spectroscopy of the intermediate compound RLS3 resulting from step 2 is shown in FIG. 3C; MS (ESI) calculated for $C_{13}H_{15}O_2$ (M+H) 203.1072, found 203.0802.

Figure 4A:
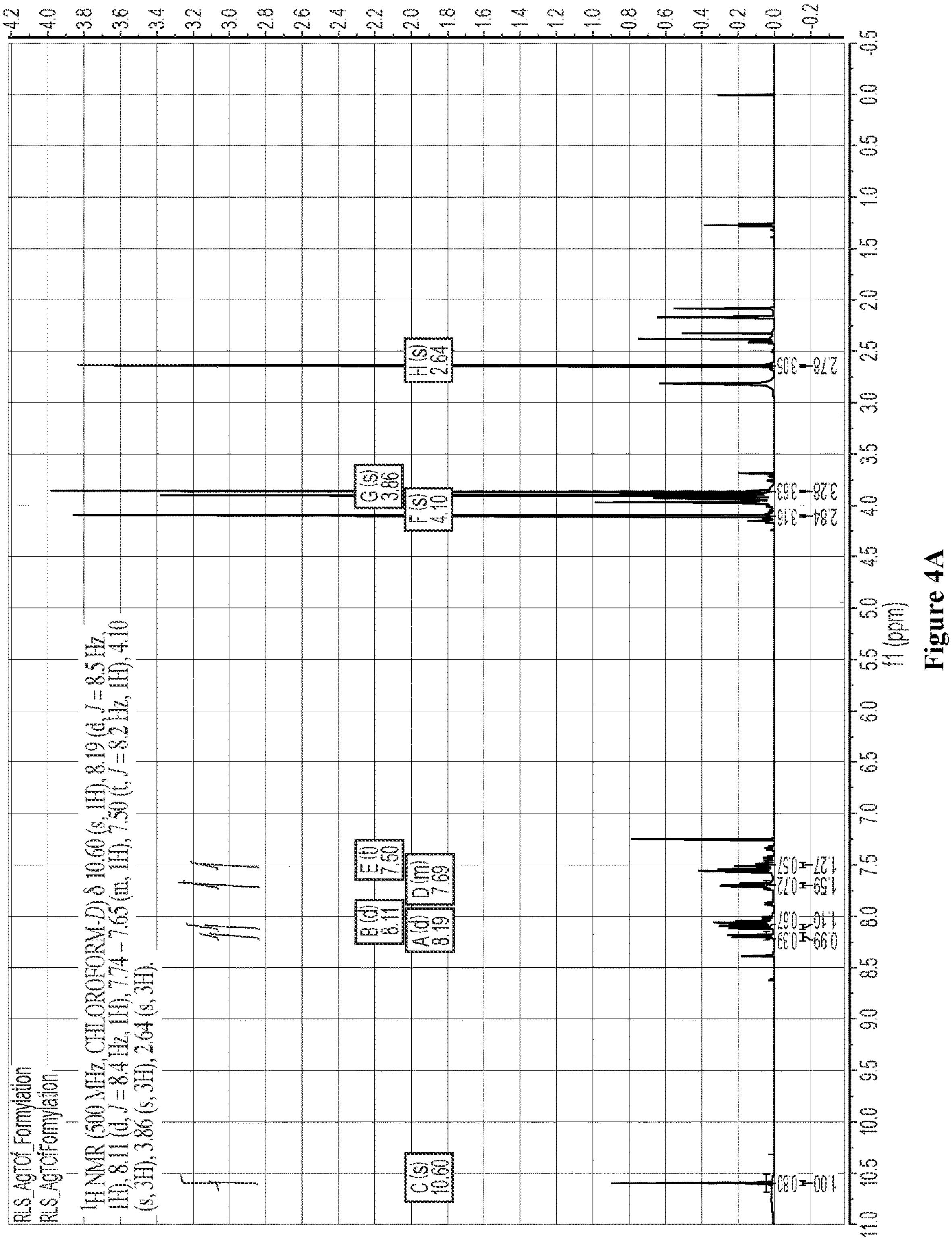
FIG. 4A is a graph that shows the $^1$H NMR for an intermediate (1,4-Dimethoxy-3-methyl-2-naphthaldehyde) of an exemplary compound of formula 1.
Figure 4B:
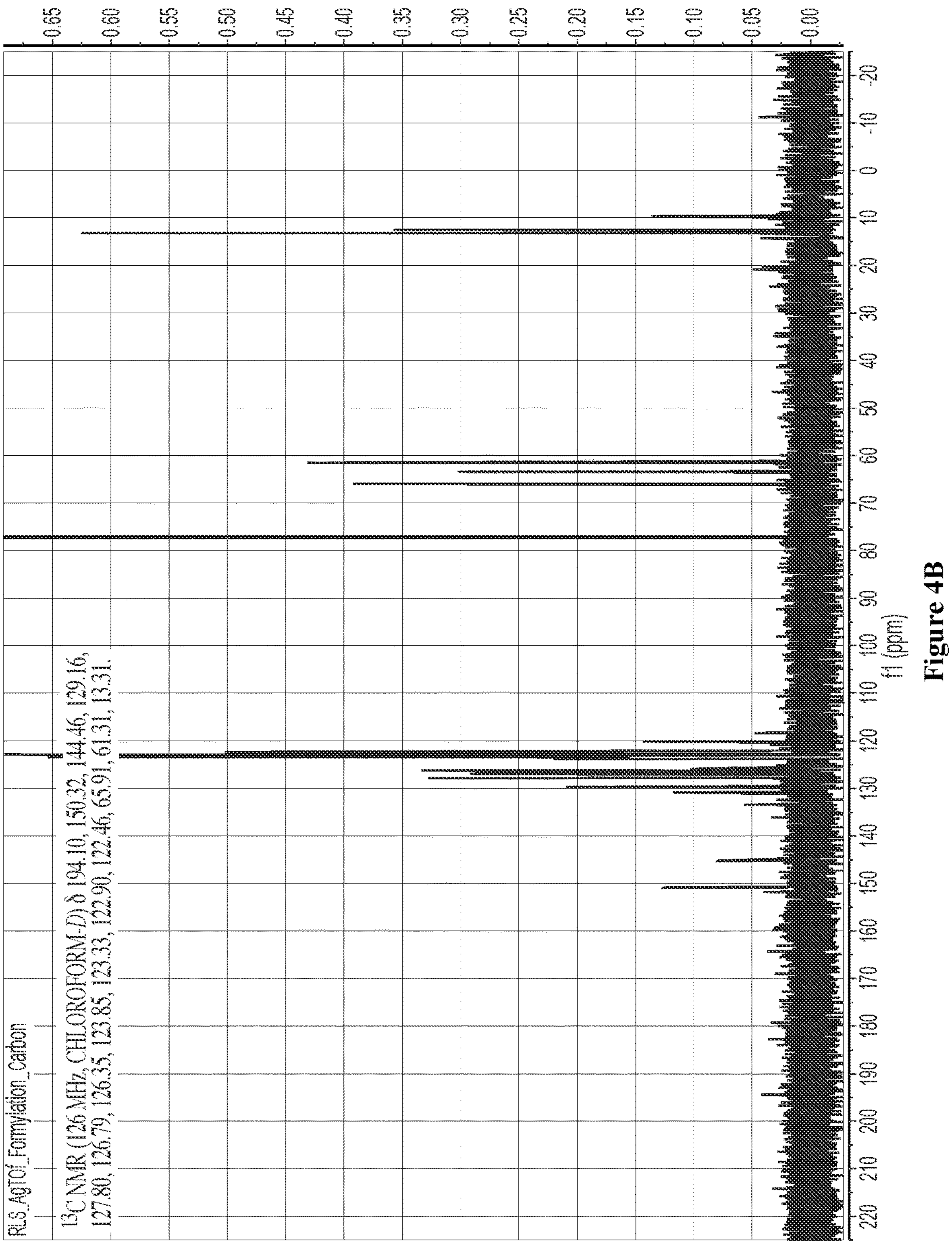
FIG. 4B is a graph that shows the $^{13}C$ NMR for an intermediate (1,4-Dimethoxy-3-methyl-2-naphthaldehyde) of an exemplary compound of formula 1.
Figure 4C:
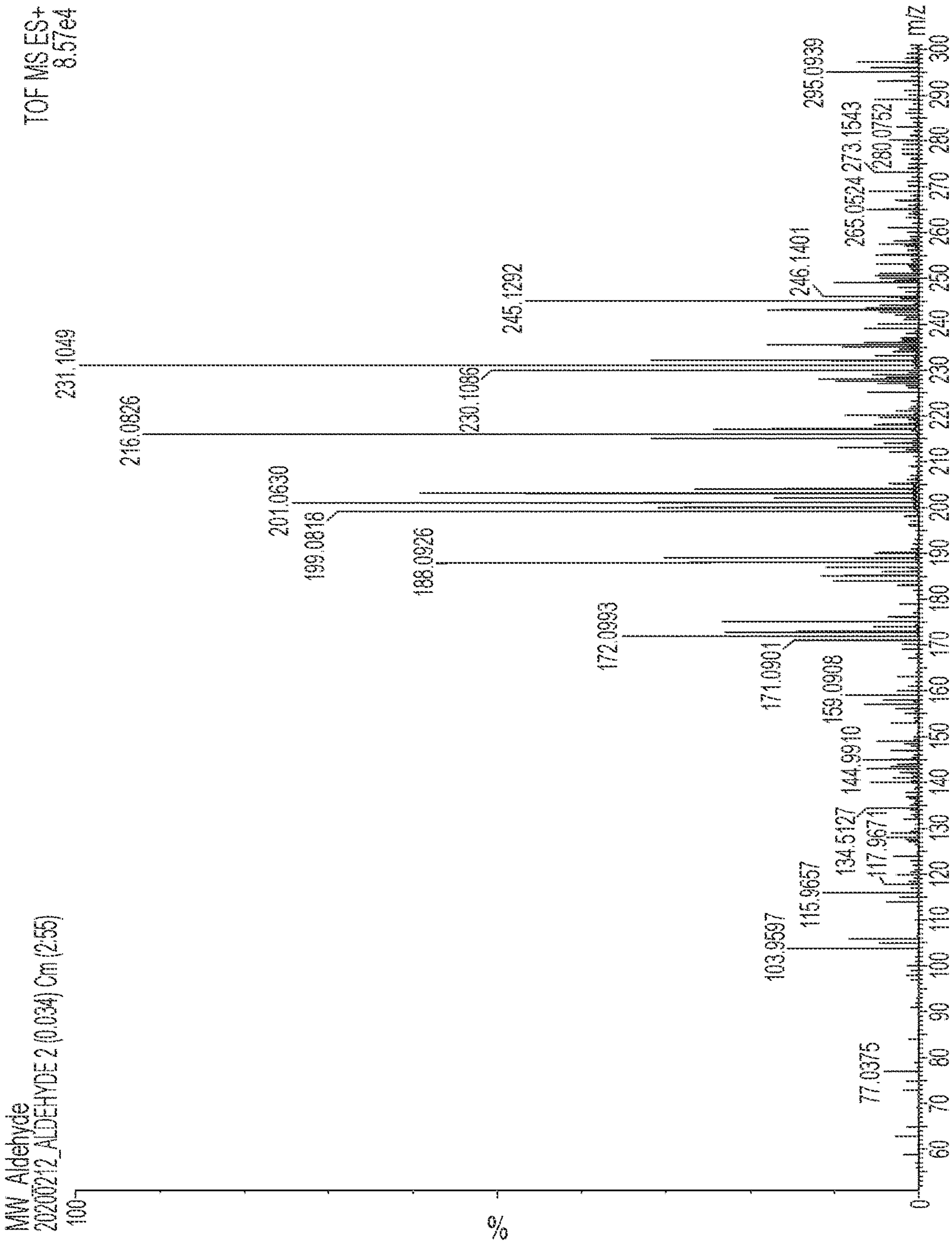
FIG. 4C is a graph that shows the Mass Spectrometry for an intermediate (1,4-Dimethoxy-3-methyl-2-naphthaldehyde) of an exemplary compound of formula 1.

$^1$H NMR spectrum of the intermediate compound RLS4 esulting from Step 3 (500 MHZ, Chloroform-D) is shown in FIG. 4A; $^1$H NMR δ 10.60 (s, 1H), 8.19 (d, J=8.5 Hz, 1H), 8.11 (d, J=8.4 Hz, 1H), 7.74-7.65 (m, 1H), 7.50 (t, J=8.2 Hz, 1H), 4.10 (s, 3H), 3.86 (s, 3H), 2.64 (s, 3H). $^{13}$C NMR spectrum of the intermediate compound RLS4 resulting from Step 3 (126 MHZ, Chloroform-D) is shown in FIG. 4B; $^{13}$C NMR (126 MHZ, CHLOROFORM-D) δ 194.10, 150.32, 144.46, 129.16, 127.80, 126.79, 126.35, 123.85, 123.33, 122.90, 122.46, 65.91, 61.31, 13.31. Mass spectroscopy of the intermediate compound RLS4 resulting from step 3 is shown in FIG. 4C; MS (ESI) calculated for $C_{14}H_{15}O_3$ (M+H) 231.1021, found 231.1049.

Figure 5A:
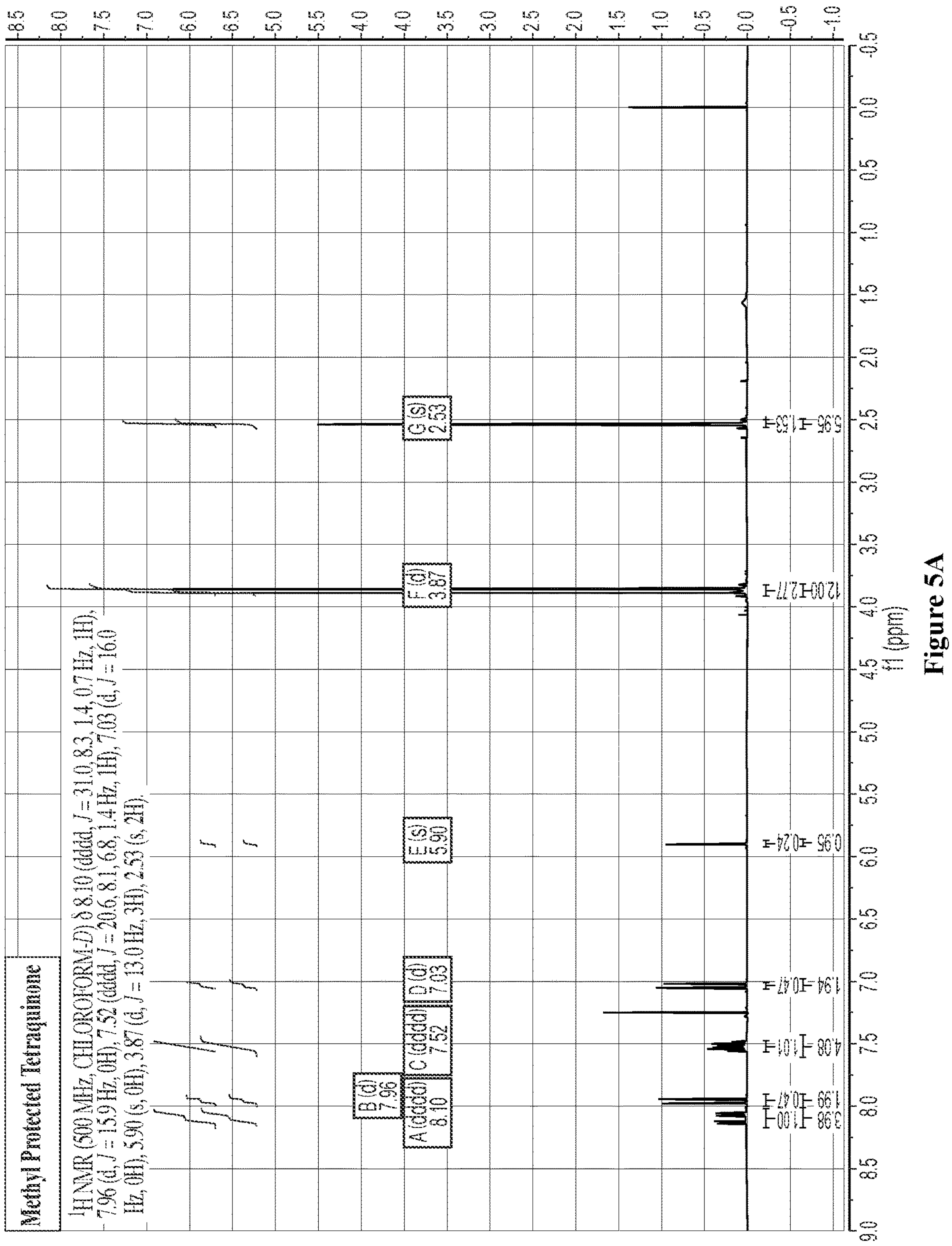
FIG. 5A is a graph that shows the $^{1}H$ NMR for an intermediate (1E,4Z,6E)-1,7-Bis(1,4-Dimethoxy-3-methylnaphthalene-2-yl)-5-Hydroxyhepta-1,4,6-trien-3-one (Dimer) of an exemplary compound of formula 1.
Figure 5B:
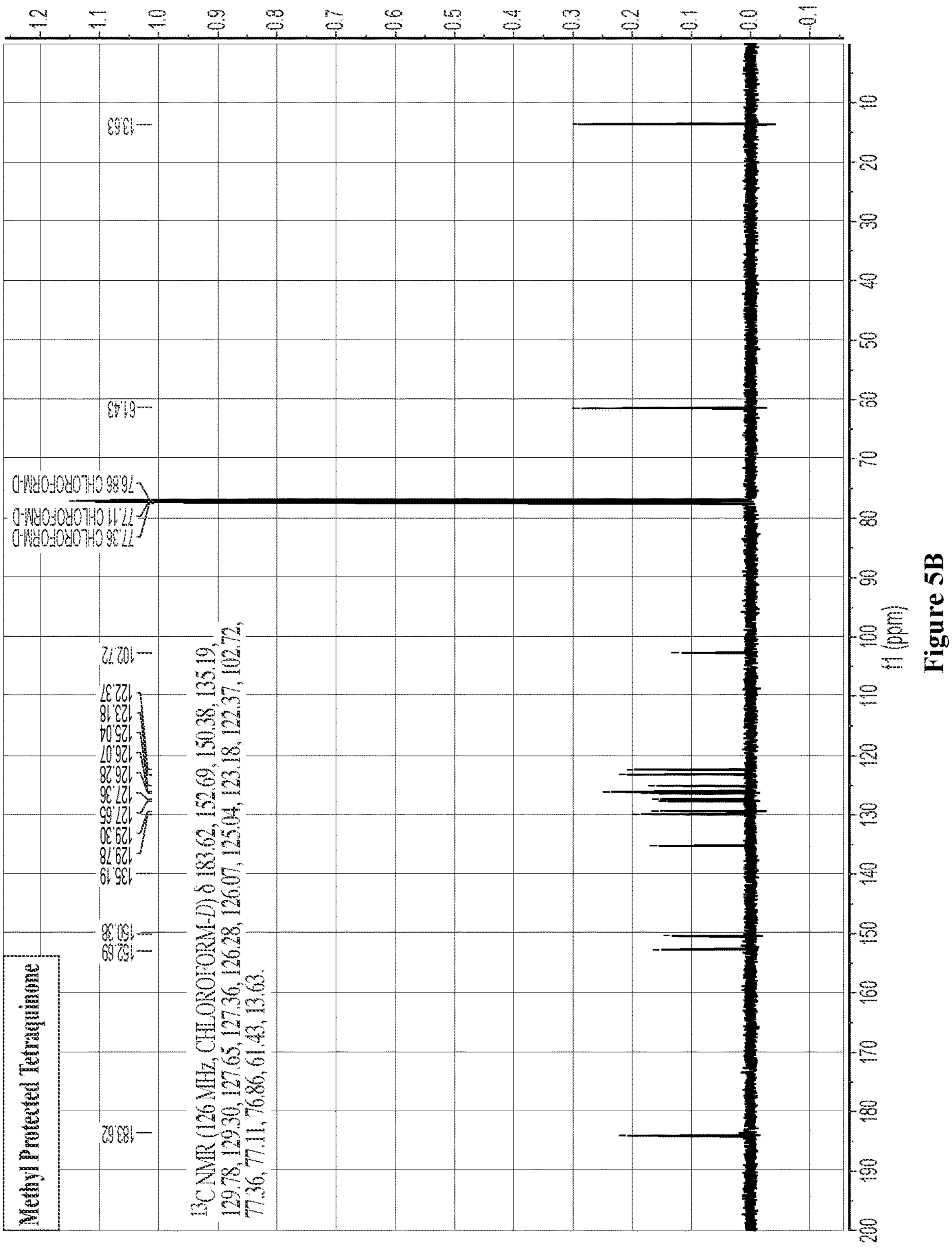
FIG. 5B is a graph that shows the $^{13}C$ NMR for an intermediate (1E,4Z,6E)-1,7-Bis(1,4-Dimethoxy-3-methylnaphthalene-2-yl)-5-Hydroxyhepta-1,4,6-trien-3-one (Dimer) of an exemplary compound of formula 1.
Figure 5C:
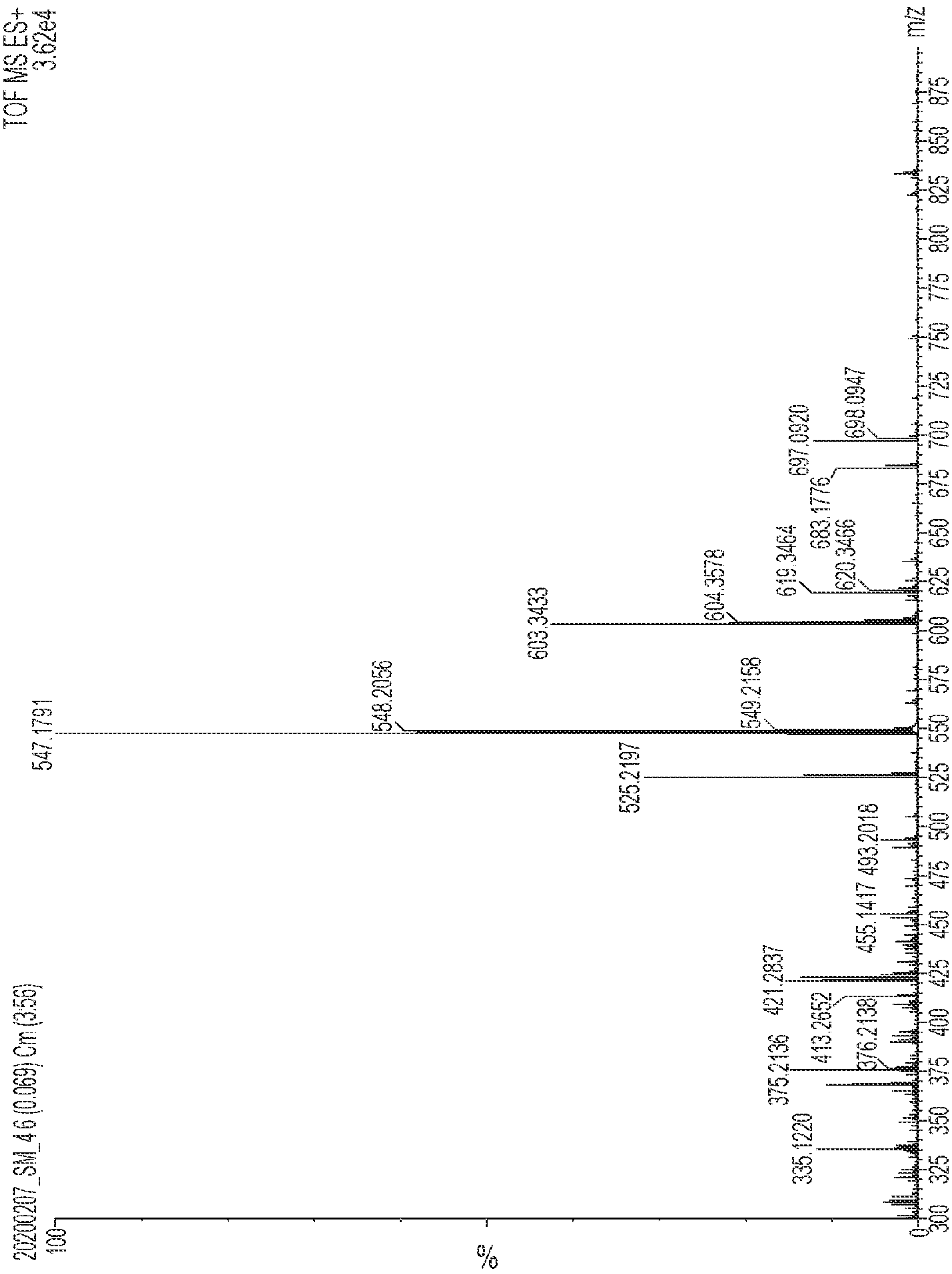
FIG. 5C is a graph that shows the Mass Spectrometry for an intermediate (1E,4Z,6E)-1,7-Bis(1,4-Dimethoxy-3-methylnaphthalene-2-yl)-5-Hydroxyhepta-1,4,6-trien-3-one (Dimer) of an exemplary compound of formula 1.

$^1$H NMR spectrum of the intermediate compound RLS5 resulting from Step 4 (500 MHz, Chloroform-D) is shown in FIG. 5A; $^1$H NMR (500 MHZ, CHLOROFORM-D) δ 8.10 (dddd, J=31.0, 8.3, 1.4, 0.7 Hz, 1H), 7.96 (d, J=15.9 Hz, 0H), 7.52 (dddd, J=20.6, 8.1, 6.8, 1.4 Hz, 1H), 7.03 (d, J=16.0 Hz, 0H), 5.90 (s, 0H), 3.87 (d, J=13.0 Hz, 3H), 2.53 (s, 2H). $^{13}$C NMR spectrum of the intermediate compound RLS5 resulting from Step 4 (126 MHZ, Chloroform-D) is shown in FIG. 5B; $^{13}$C NMR (126 MHZ, CHLOROFORM-D) δ 183.62, 152.69, 150.38, 135.19, 129.78, 129.30, 127.65, 127.36, 126.28, 126.07, 125.04, 123.18, 122.37, 102.72, 77.36, 77.11, 76.86, 61.43, 13.63. Mass spectroscopy of the intermediate compound RLS5 resulting from step 4 is shown in FIG. 5C; HRMS (ESI) calculated for $C_{33}H_{33}O_6$ (M+H) 525.2277, found 525.2197.

Figure 6A:
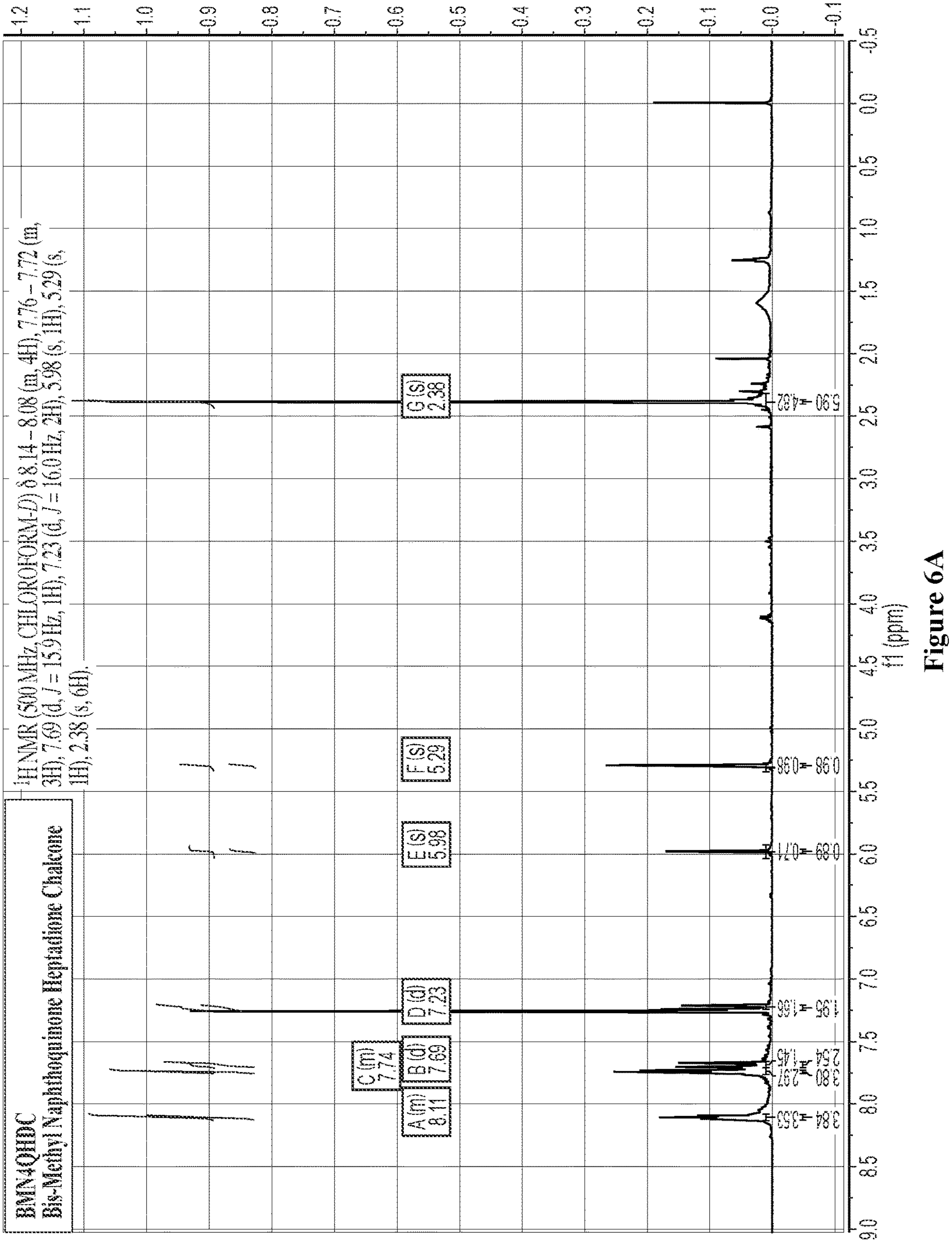
FIG. 6A is a graph that shows the $^{1}H$ NMR for an exemplary compound of formula 1 (3,3'-((1E,3Z,6E)-3-Hydroxy-5-Oxohepta-1,3,6-triene-1,7-diyl)Bis(2-Methylnapthalene-1,4-Dione).
Figure 6B:
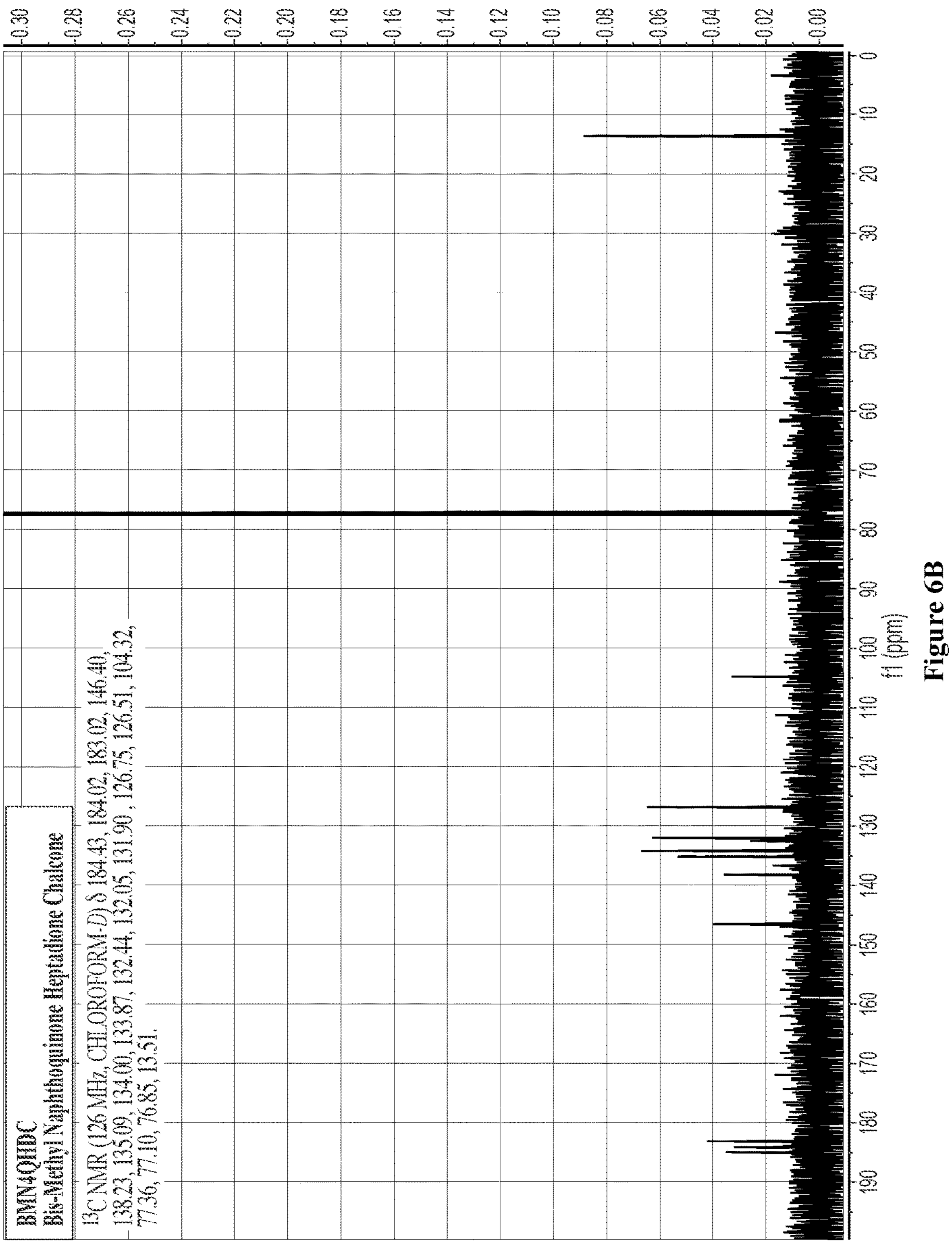
FIG. 6B is a graph that shows the $^{13}C$ NMR for an exemplary compound of formula 1 (3,3'-((1E,3Z,6E)-3-Hydroxy-5-Oxohepta-1,3,6-triene-1,7-diyl)Bis(2-Methylnapthalene-1,4-Dione).
Figure 6C:
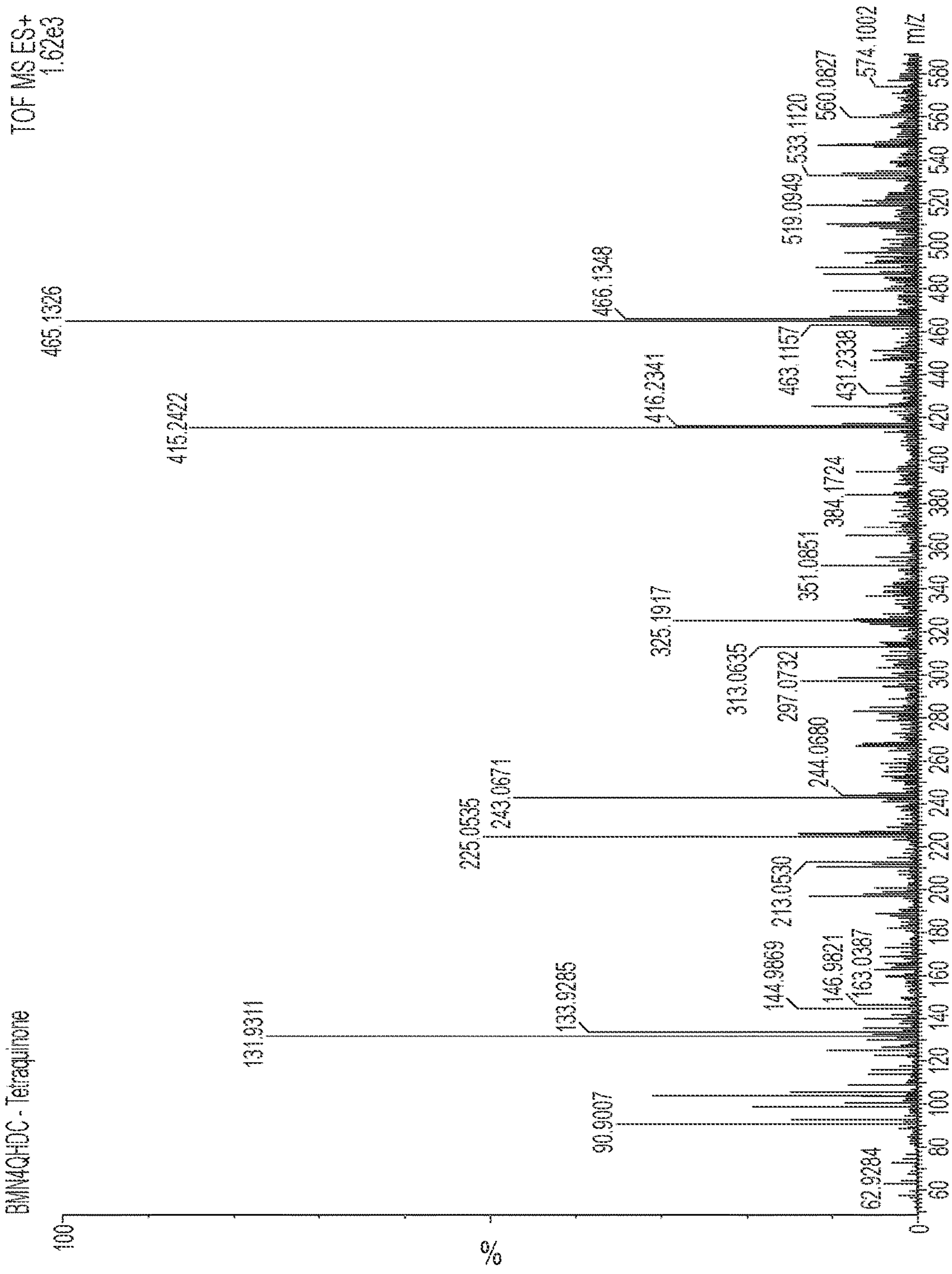
FIG. 6C is a graph that shows the Mass Spectrometry for an exemplary compound of formula 1 (3,3'-((1E,3Z,6E)-3-Hydroxy-5-Oxohepta-1,3,6-triene-1,7-diyl)Bis(2-Methylnapthalene-1,4-Dione).

$^1$H NMR spectrum of the final compound RLS6 Enol from step 5 (500 MHZ, Chloroform-D) is shown in FIG. 6A; $^1$H NMR δ 8.14-8.10 (m, 4H), 7.77-7.73 (m, 4H), 7.69 (d, J=15.9 Hz, 2H), 7.24 (d, J=16.0 Hz, 2H), 5.99 (s, 1H), 5.30 (s, 1H), 2.39 (s, 6H). $^{13}$C NMR spectrum of the final compound RLS6 Enol from step 5 (126 MHZ, Choloform-D) is shown in FIG. 6B; $^{13}$C NMR δ 184.43, 184.02, 183.02, 146.40, 138.23, 135.09, 134.00, 133.87, 132.44, 132.05, 131.90, 126.75, 126.51, 104.32, 77.36, 77.10, 76.85, 13.51. Mass spectroscopy of the final compound RLS6 Enol rom step 5 is shown in FIG. 6C; HRMS (ESI) calculated for $C_{29}H_{20}O_6$ (M+H) 465.1338, found 465.1326.

Example 2 Effect of R-Substituted Naphthoquinone-Based Chalcone Derivatives and Intermediates on Cellular Metabolic Activity To determine effects on cellular metabolic activity as a measure of efficacy, the menadione derivative Dimenadione Curcumin RLS6 or intermediates RLS3, RLS4, and RLS5 were tested in autobioluminescent HEK 293, HepG2 and Astrocyte cells and results are shows in FIGS. 7A, 7B, 8A, 8B and 9. 5 fM to 5 μM (10 μL/well) of individual compounds solubilized in DMSO were incubated with cells in 96-well plates. The reference compound was DMSO-only vehicle control, at a final concentration of 0.1% DMSO. Importantly maximally effective concentrations of the compound, in the mid-picomolar to mid-nanomolar range, increased metabolic activity by as much as 2.5-fold. This observation aligns with the core hypothesized mechanism of the compound which has been designed to integrate into the mitochondrial ETC and improve energy production in the form of ATP in mitochondria. Increased energy production is reflected in overall cellular metabolism of the cells.

Figure 7A:
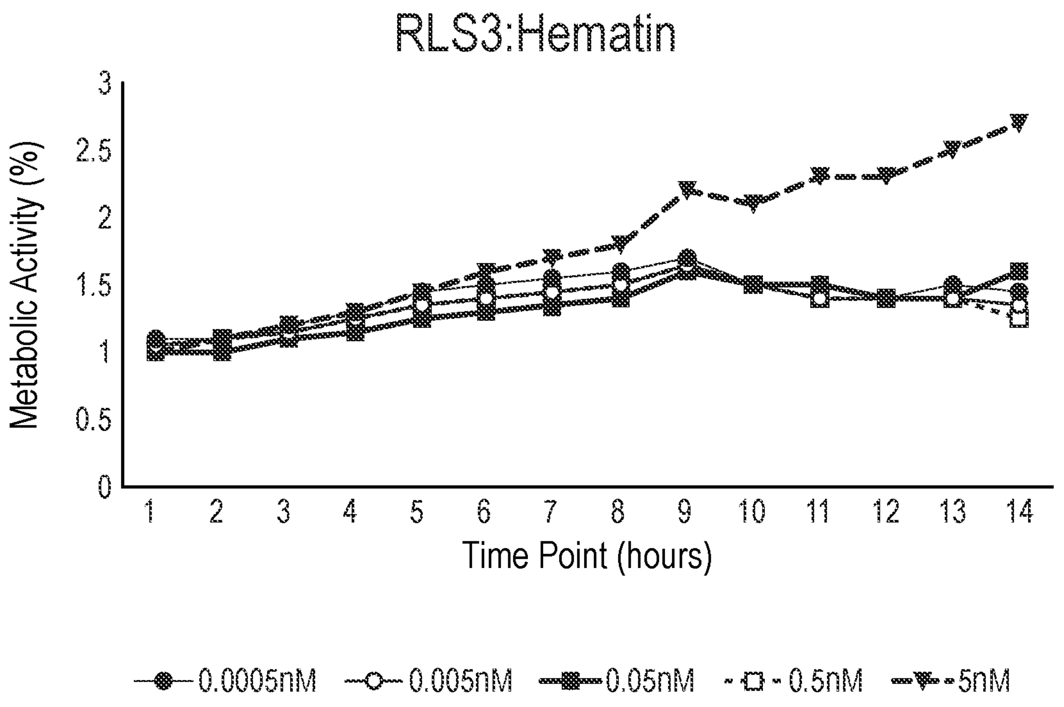
FIG. 7A is a graph that shows the metabolic activity in kidney (renal) cells for an intermediate (RLS3) of an exemplary compound of formula 1 given at different concentrations ranging from 0.5 pM to 5 nM RLS3 (Ratio Hematin: RLS3 1:1000).
Figure 7B:
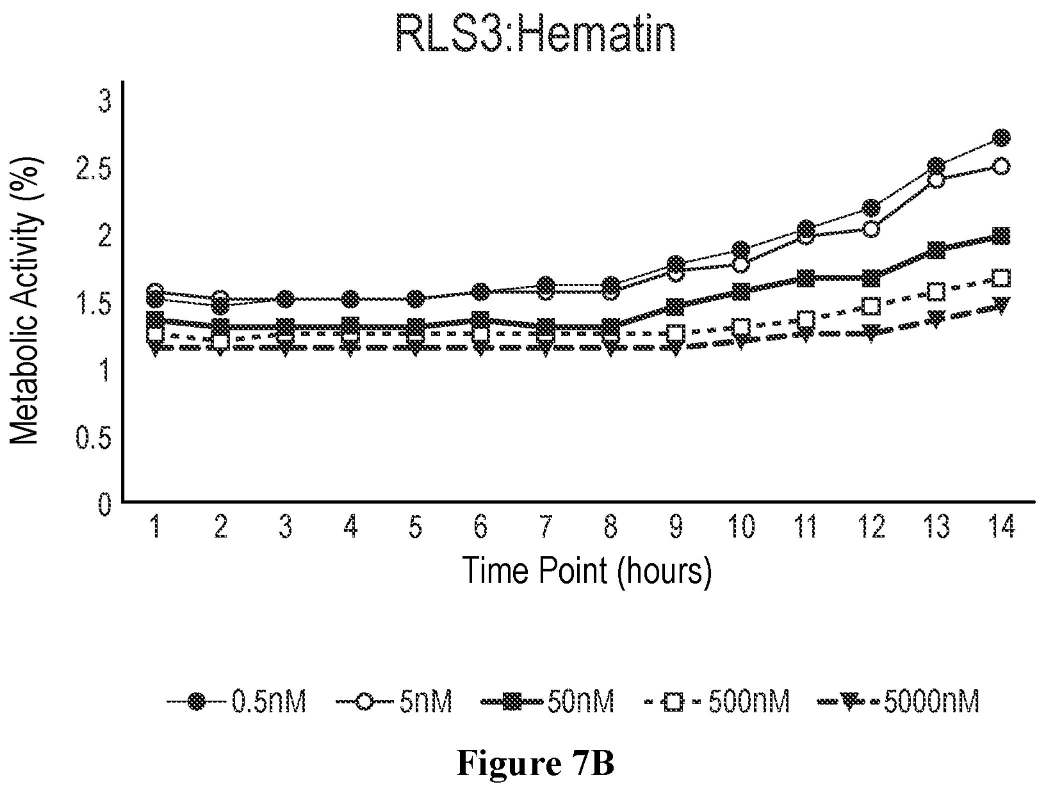
FIG. 7B is a graph that shows the metabolic activity in kidney (renal) cells for an intermediate (RLS3) of an exemplary compound of formula 1 given at different concentrations ranging from 0.5 nM to 5 μM RLS3 (Ratio Hematin: RLS3 1:1000).

FIG. 7A shows toxicity screens for Hematin:RLS3 (1:1,000) (0.5 pM-5 nM RLS(x) 3) using an autobioluminescent kidney cell model to monitor metabolic impacts over a 14-hour period post-exposure. Kidney cells exposed to RLS3 in combination with Hematin showed an increase in metabolic activity over time. FIG. 7B shows toxicity screens for Hematin:RLS3 (1:1,000) (500 pM-5 μM RLS (x) 3) using an autobioluminescent liver cell model to monitor metabolic impacts over a 14 h period post-exposure. Treatment with RLS3 mixed with hematin showed an increase in metabolic activity over time.

Figure 8A:
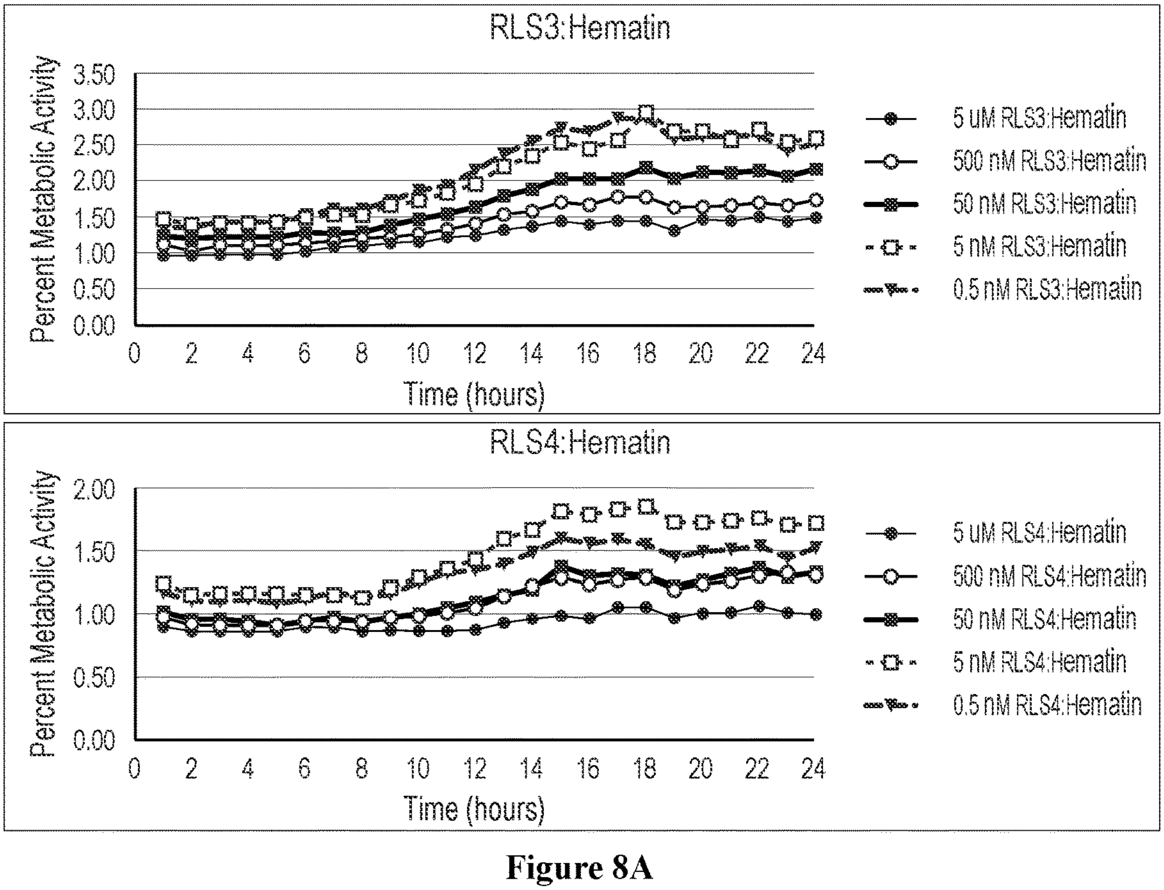
FIG. 8A are two graphs that show the metabolic activity in liver (hepatic) cells for intermediates (RLS3 and RLS4) of an exemplary compound of formula 1 given at different concentrations ranging from 0.5 nM to 5 μM RLSx and complexed with hematin (Ratio Hematin:RLSx 1:1000).
Figure 8B:
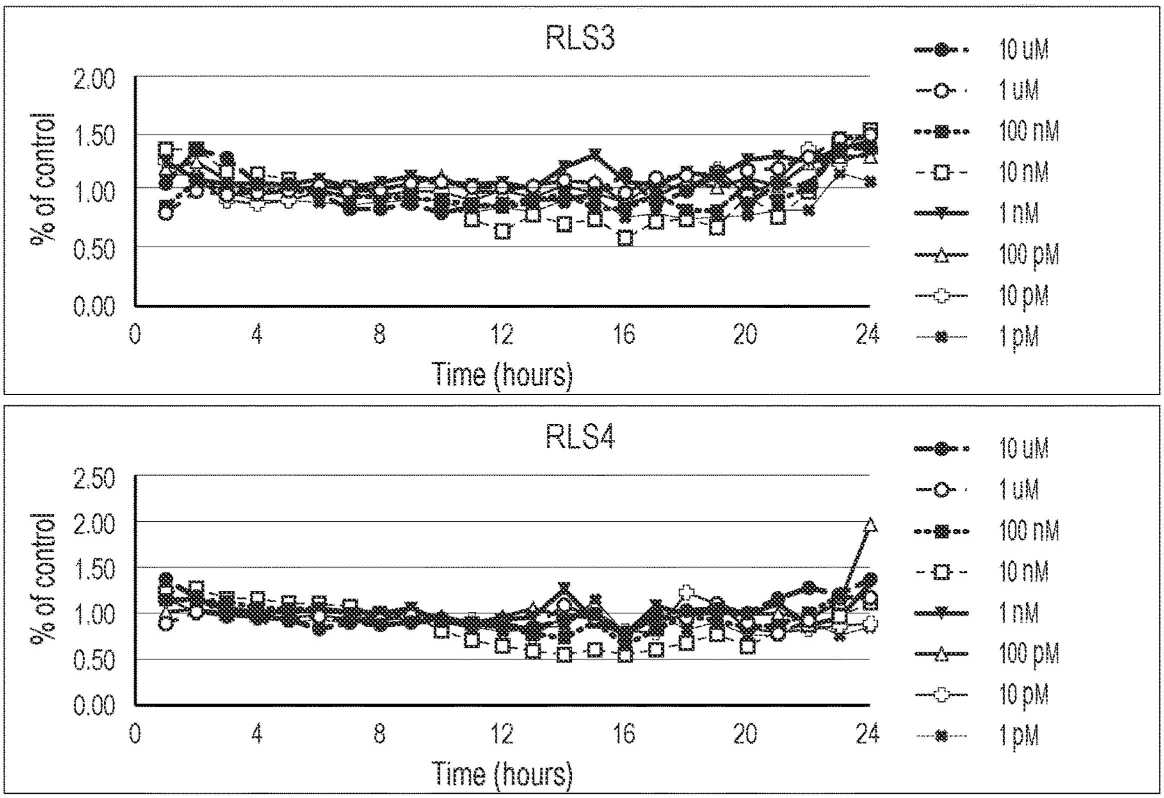
FIG. 8B are two graphs that show the metabolic activity in liver (hepatic) cells for intermediates (RLS3 and RLS4) of an exemplary compound of formula 1 given at different concentrations ranging from 1.0 pM to 10 μM RLSx without complexing with hematin.

FIG. 8A shows toxicity screens for Hematin:RLS3 or RLS4 (1:1,000 ratio) at concentrations ranging from (0.5 nM-5 μM RLS (x)) using an autobioluminescent liver cell model to monitor metabolic impacts over a 24-hour period post-exposure. Liver cells exposed to RLS3 or RLS4 complexed with Hematin showed an increase in metabolic activity over time. FIG. 8B shows toxicity screens for RLS3 and RLS4 without hematin at concentrations ranging from (1 pM-10 μM RLS (x)) using an autobioluminescent liver cell model to monitor metabolic impacts over a 24 h period post-exposure. Treatment with either RLS3 or RLS4 complexed with hematin seemed to show a concentration-dependent effect on cellular metabolism over time while compounds without hematin complexation did not.

Figure 9A:
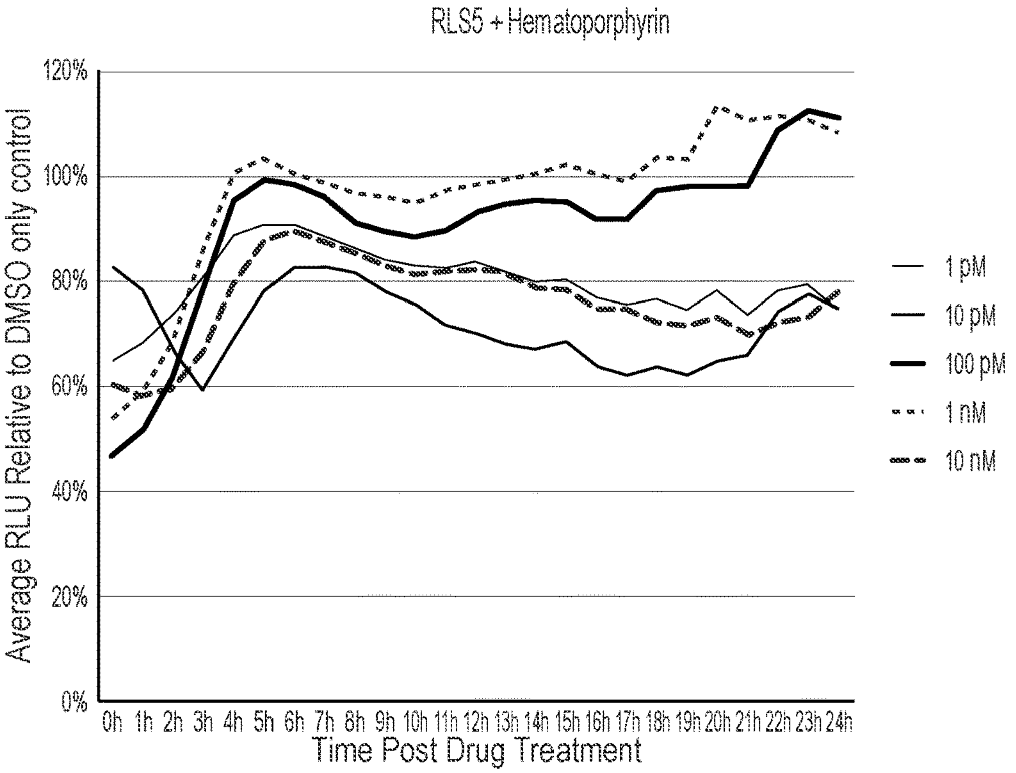
FIG. 9A is a graph that shows the metabolic activity in neuronal (astrocyte) cells for an intermediate (RLS5) of an exemplary compound of formula 1 given at different concentrations ranging from 1.0 pM to 10 nM RLS5 and complexed with hematoporphyrin (Ratio Hematoporphyrin: RLS5 1:1000).
Figure 9B:
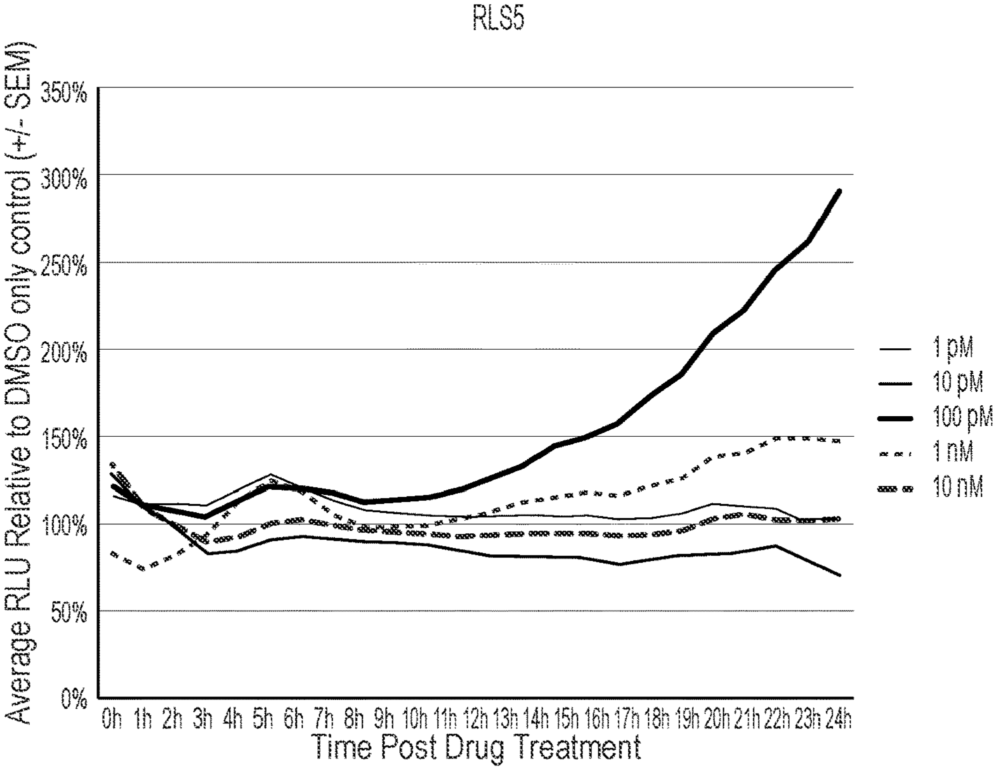
FIG. 9B is a graph that shows the metabolic activity in neuronal (astrocyte) cells for an intermediate (RLS5) of an exemplary compound of formula 1 given at different concentrations ranging from 1.0 pM to 10 nM RLS5.

FIG. 9A shows toxicity screens for RLS5/Compound 1A metabolic activity in neuronal (astrocyte) cells given at different concentrations ranging from 1.0 pM to 10 nM RLS5/Compound 1A (Ratio Hematoporphyrin:RLS5/Compound 1A 1:1000) using an autobioluminescent neuronal cell model to monitor metabolic impacts over a 24 hour period post-exposure. FIG. 9B shows toxicity screens for RLS5 metabolic activity in neuronal (astrocyte) cells given at different concentrations ranging from 1.0 pM to 10 nM RLS5 using an autobioluminescent neuronal cell model to monitor metabolic impacts over a 24 hour period post-exposure. Treatment with 100 pM and 1 nM RLS5 (with and without complexation with Hematoporphyrin) had a slight concentration dependent effect on cellular metabolism. The astrocytes used in these assays are primary cells, harvested from murine cerebral cortex (or forebrain from cerebral hemisphere) and are assumed to be protoplasmic Type I astrocytes. These are not an immortalized cell line, in an effort to better reflect in vivo cell phenotypes.

Example 3 Effect of Formulation and Temperature on Stability of R-Substituted Naphthoquinone-Based Chalcone Derivatives and Intermediates The objective of this study was to determine the stability and degradation of SNC1 (RLS5 formulated in PEG200 or PEG200 in 10% aqueous ethanol) or Bulk Drug Substance (BDS) in DMSO at room temperature and 4° C. All test materials were aliquoted in sufficient quantities to perform testing in triplicate to eliminate any sampling bias. All test time points were analyzed by LC/MS (Agilent 1200 infinity series with Diode Array Detector DAD). Stability testing for any storage condition was discontinued if two successive stability test points failed. Stability testing was performed daily for the first 5 days following $T_0$ and then after the first 5 days at weeks 2, 3 and 4 for the first month and then monthly thereafter the first month. The following stability samples were prepared: S2-SNC1 in PEG200 (2 mg/ml) stored at room temperature; S3-SNC1 in PEG200/10% ethanol (2 mg/ml) stored at room temperature; S4-SNC1 in PEG200 (2 mg/ml) stored at 2-8° C.; S5-SNC1 in PEG200/10% ethanol (2 mg/ml) stored at 2-8° C. and S6-SNC1 in DMSO at room temperature. Appearance of Samples S2 and S4 showed they had formed a precipitate while S3 and S5 had less precipitate and S6 stayed dissolved in DMSO.

Figure 10:
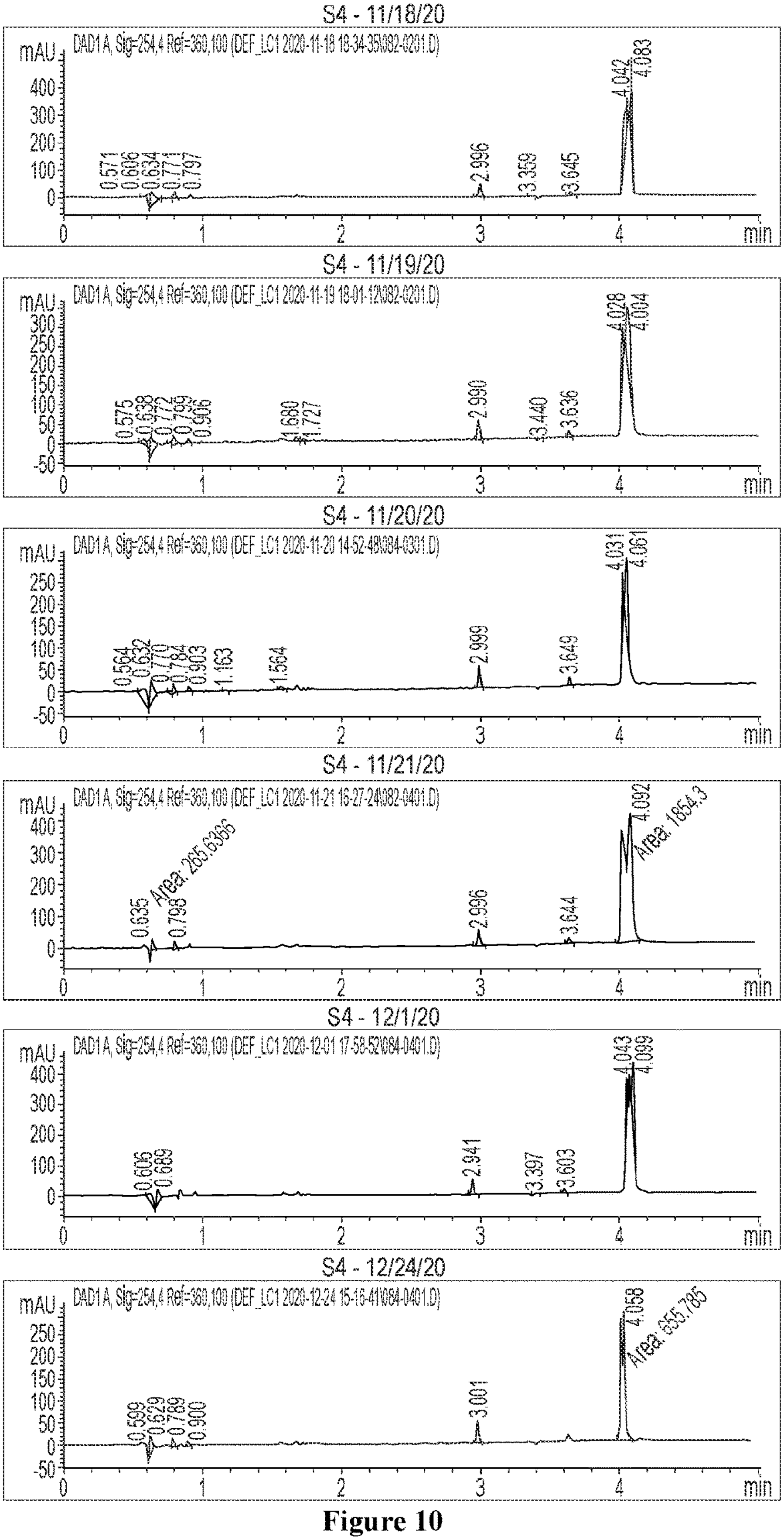
FIG. 10 shows stability data for a stable formulation of an intermediate (RLS5) of an exemplary compound of formula 1 in polyethylene glycol (PEG200) with and without 10% ethanol at various time points and temperatures assessed by LC/MS.

The LCMS was not optimized and therefore peaks were broad and contained shoulders despite the lack of a uniform peak the mass detected corresponded to SNC1. Samples S3 and S5 had low intensity and were difficult to see impurities at low concentrations. Sample S2-SNC1 was the major peak with a retention time (rt) of 4.05 min while three impurities or degradation products of significance had minor peaks at 2.7, 2.9 and 3.6 min which increased over time (data not shown). Sample S4-SNC1 was the major peak with a retention time (rt) of 4.05 min while three impurities had minor peaks at 2.7, 2.9 and 3.6 min which did not seem to change from the one time point to the next (see FIG. 10 for LCMS traces for 6 time points). Sample S6-SNC1 was the major peak again with an retention time (rt) of 4.05 min but with two major impurity peaks at 2.9 and 3.6 min that did not change significantly over time. Storage of SNC1 in DMSO at lower temperatures may be a strategy for storing a solution of the API. The following table shows the percentage of material remaining from the different stability samples over time and indicates that SNC1 formulated in PEG200 alone stored at 2-8° C. shows good stability (little quantifiable degradation of the main SNC1 peak) for up to 2 months.

TABLE 1

| Percent SNC1 Stability Samples Remaining Over Time | | | | |
|---|---|---|---|---|
| Date | T = Time | S2 | S4 | S6 |
| Nov. 18, 2020 | 24 hours | 93% | 95% | 88% |
| Nov. 20, 2020 | 72 hours | 93% | 95% | — |
| Nov. 21, 2020 | 4 days | 96% | 95% | 84% |
| Dec. 1, 2020 | ~2 weeks | 93% | 95% | 80% |
| Dec. 24, 2020 | ~4 weeks | 78% | 91% | 81% |
| Jan. 22, 2021 | ~8 weeks | 72% | 94% | 81% |

Figure 11:
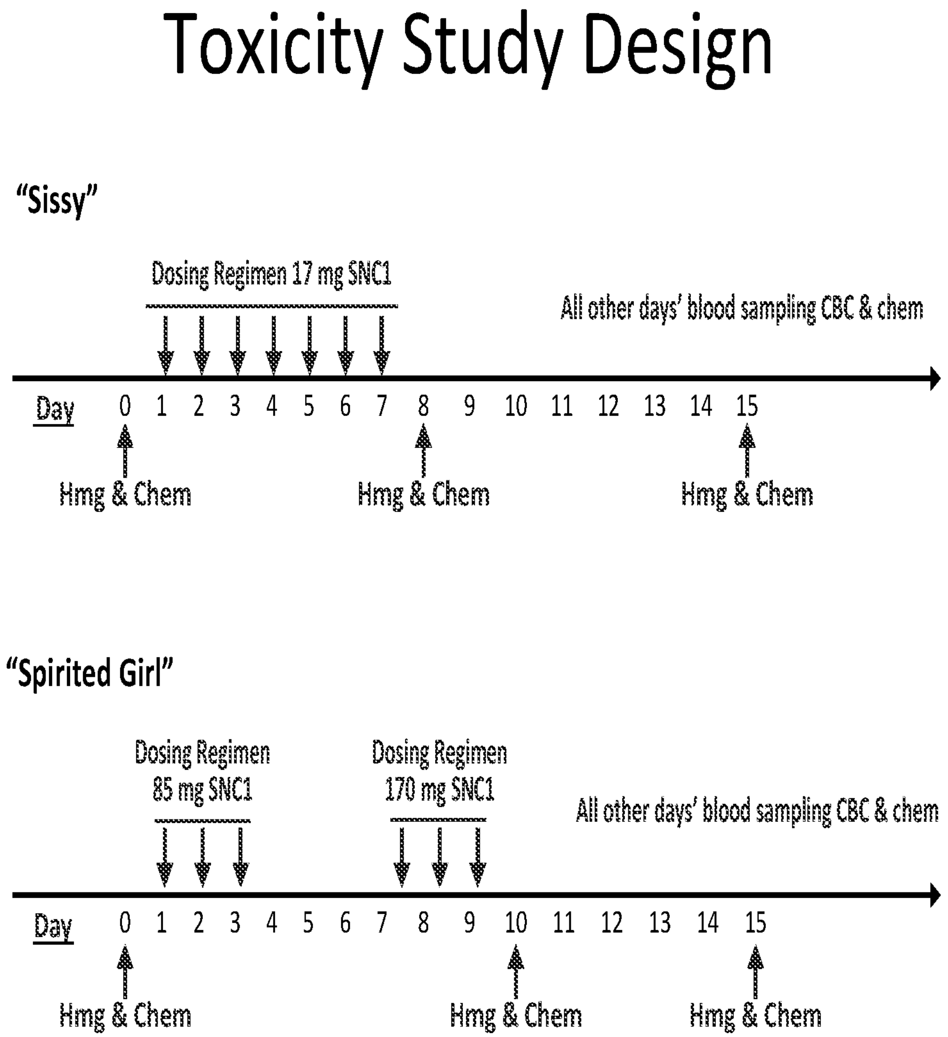
FIG. 11 shows a diagram of the toxicity study performed on two naïve horses treated with various doses of SNC1 (polyethylene glycol (PEG200) formulated RLS5).

Example 4 Toxicity of R-Substituted Naphthoquinone-Based Chalcone Derivatives and Intermediates at Three Different Doses on Naïve Animals The objective of this study was to determine the toxicity and tolerability of SNC1 (RLS5 formulated in PEG200 and 10% aqueous ethanol). All test materials were aliquoted in sufficient quantities to perform three tests. Serum chemistries and complete hemograms (Hmg) or complete blood counts (CBC) were performed on various test days as in FIG. 11. The following outlines the Toxicity Study Design depicted in FIG. 11:

1. 17 mg SNC1 in PEG 200 and 10% aqueous ethanol
   - 0.06 mg SNC1/mL PEG 200-10% ethanol diluted into 1.5 L lactated Ringer's solution (LRS)
   - Administered by IV once daily for 7 days
   - Hmg and serum chemistries tested at baseline and on days 8 and 15
   - CBC and serum chemistries tested daily on days 1-7
2. 85 mg SNC1 in PEG 200 and 10% aqueous ethanol
   - 0.3 mg SNC1/mL PEG 200-10% ethanol diluted into 5 L LRS
   - Administered by IV once daily for 3 days
   - Hmg and serum chemistries tested at baseline and on days 4 and 11
   - CBC and serum chemistries tested daily on days 1-3
3. 170 mg SNC1 in PEG 200 and 10% aqueous ethanol
   - 0.6 mg SNC1/mL PEG 200-10% ethanol diluted into 10 L LRS
   - Administered by IV once daily for 3 days
   - Hmg and serum chemistries tested at baseline and on days 4 and 11
   - CBC and serum chemistries tested daily on days 1-3

All three doses of SNC1 in polyethylene glycol and ethanol tested were well tolerated by the animals. No remarkable signs of toxicity were observed, and no significant abnormal changes in serum chemistries, hmgs or CBCs were noted. The SNC1/PEG-200/10% ethanol solution was observed to form an emulsion when diluted into Lactated Ringer's Solution (LRS), particularly at the higher concentrations. Some residual compound was observed in the LRS bags and IV lines, so actual dosing may have been slightly less than calculated.

Figure 12:
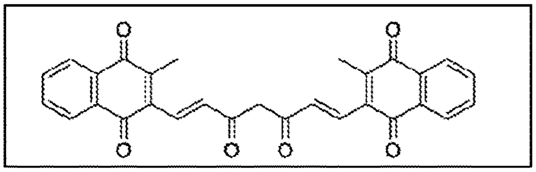
FIG. 12 is a diagram of RLSx intermediates and final compound nomenclature and chemical structures.
Figure 12:
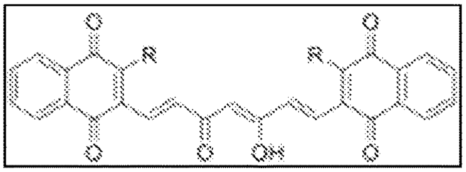
Figure 12:
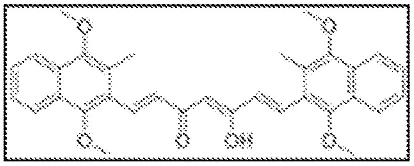
Figure 12:
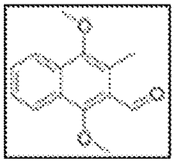
Figure 12:
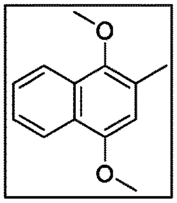
Figure 12:
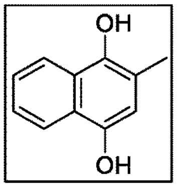
Figure 13:
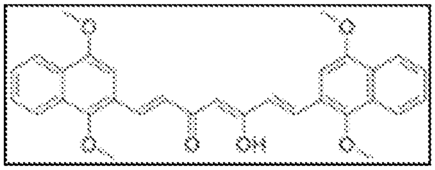
FIG. 13 is a diagram of RLSx analogues nomenclature and chemical structures.
Figure 13:
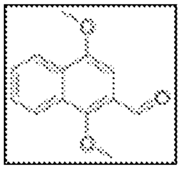
Figure 13:
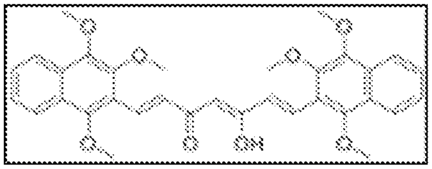
Figure 13:
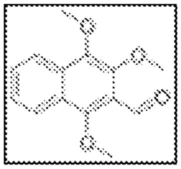

In FIG. 12 is a chart of the various RLSx intermediate and final compounds, nomenclature and chemical structures including RLS2, RLS3, RLS4, RLS5, RLS6 Enol and RLS6. In FIG. 13 is a chart of the various RLSx related analogues and intermediates nomenclature and chemical structures either demethylated or with a methoxy substituent in 2 position on naphthalene ring.

It is intended that the specification and above-described examples be considered as exemplary only. Other embodiments including alterations, modifications and variations to the particular examples will be apparent to those of skill in the art from a consideration of the specification or practice of the compounds, compositions and methods disclosed herein, without departing from the scope, which is defined solely by the claims appended hereto.

What is claimed is:

1. A composition comprising: a compound of formula 1

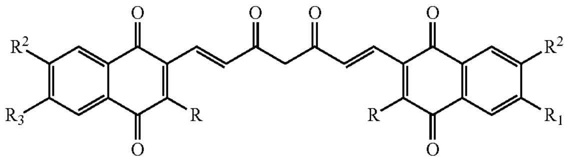

wherein:

R is —H, —$CH_3$, —$C_2H_5$, alkyl —$C_nH_2n+1$ (where n is an integer from 3-x), or —OH;

R1 and R2 are independently —H, —$CH_3$, —$C_2H_5$, —$OCH_3$, alkyl —$C_nH_2n+1$ (where n is an integer from 3 to x), —OH, phenyl —$C_6H_5$, naphthyl, or an amino acid.

2. The composition comprising a compound of claim 1 having:
(a) R selected from —H, and R1 and R2 selected from —H;
(b) R selected from —H, and R1 and R2 selected from —$CH_3$;
(c) R selected from —H, and R1 and R2 selected from —$C_2H_5$;
(d) R selected from —H, and R1 and R2 selected from —$OCH_3$;
(e) R selected from —H, and R1 and R2 selected from alkyl —$C_nH_2$n+1 (where n is an integer from 3-x);
(f) R selected from —H, and R1 and R2 selected from —OH;
(g) R selected from —H, and R1 and R2 selected from phenyl —$C_6H_5$;
(h) R selected from —H, and R1 and R2 selected from naphthyl; or
(i) R selected from —H, and R1 and R2 selected from an amino acid.

3. The composition comprising a compound of claim 1 having:
(a) R selected from —$CH_3$, and R1 and R2 selected from —H;
(b) R selected from —$CH_3$, and R1 and R2 selected from —$CH_3$;
(c) R selected from —$CH_3$, and R1 and R2 selected from —$C_2H_5$;
(d) R selected from —$CH_3$, and R1 and R2 selected from —$OCH_3$;
(e) R selected from —$CH_3$, and R1 and R2 selected from alkyl —$C_nH_2$n+1 (where n is an integer from 3-x)
(f) R selected from —$CH_3$, and R1 and R2 selected from —OH;
(g) R selected from —$CH_3$, and R1 and R2 selected from phenyl —$C_6H_5$;
(h) R selected from —$CH_3$, and R1 and R2 selected from naphthyl; or
(i) R selected from —$CH_3$, and R1 and R2 selected from an amino acid.

4. The composition comprising a compound of claim 1 having:
(a) R selected from —$C_2H_5$, and R1 and R2 selected from —H;
(b) R selected from —$C_2H_5$, and R1 and R2 selected from —$CH_3$;
(c) R selected from —$C_2H_5$, and R1 and R2 selected from —$C_2H_5$;
(d) R selected from —$C_2H_5$, and R1 and R2 selected from —$OCH_3$;
(e) R selected from —$C_2H_5$, and R1 and R2 selected from alkyl —$C_nH_2$n+1 (where n is an integer from 3-x)
(f) R selected from —$C_2H_5$, and R1 and R2 selected from —OH;
(g) R selected from —$C_2H_5$, and R1 and R2 selected from phenyl —$C_6H_5$;
(h) R selected from —$C_2H_5$, and R1 and R2 selected from naphthyl; or
(i) R selected from —$C_2H_5$, and R1 and R2 selected from an amino acid.

5. The composition comprising a compound of claim 1 having:
(a) R selected from alkyl —$C_nH_2$n+1 (where n is an integer from 3-x), and R1 and R2 selected from —H;
(b) R selected from alkyl —$C_nH_2$n+1 (where n is an integer from 3-x), and R1 and R2 selected from —$CH_3$;
(c) R selected from alkyl —$C_nH_2$n+1 (where n is an integer from 3-x), and R1 and R2 selected from —$C_2H_5$;
(d) R selected from alkyl —$C_nH_2$n+1 (where n is an integer from 3-x), and R1 and R2 selected from —$OCH_3$;
(e) R selected from alkyl —$C_nH_2$n+1 (where n is an integer from 3-x), and R1 and R2 selected from alkyl —$C_nH_2$n+1 (where n is an integer from 3-x);
(f) R selected from alkyl —$C_nH_2$n+1 (where n is an integer from 3-x), and R1 and R2 selected from —OH;
(g) R selected from alkyl —$C_nH_2$n+1 (where n is an integer from 3-x), and R1 and R2 selected from phenyl —$C_6H_5$;
(h) R selected from alkyl —$C_nH_2$n+1 (where n is an integer from 3-x), and R1 and R2 selected from naphthyl; or
(i) R selected from alkyl —$C_nH_2$n+1 (where n is an integer from 3-x), and R1 and R2 selected from an amino acid.

6. The composition comprising a compound of claim 1 having:
(a) R selected from —OH, and R1 and R2 selected from —H;
(b) R selected from —OH, and R1 and R2 selected from —$CH_3$;
(c) R selected from —OH, and R1 and R2 selected from —$C_2H_5$;
(d) R selected from —OH, and R1 and R2 selected from —$OCH_3$;
(e) R selected from —OH, and R1 and R2 selected from alkyl —$C_nH_2$n+1 (where n is an integer from 3-x);
(f) R selected from —OH, and R1 and R2 selected from —OH;
(g) R selected from —OH, and R1 and R2 selected from phenyl —$C_6H_5$
(h) R selected from —OH, and R1 and R2 selected from naphthyl; or
(i) R selected from —OH, and R1 and R2 selected from an amino acid.

7. The composition comprising a compound of claim 1 having R selected from —H and R1 and R2 independently selected from —H, —$CH_3$, —$C_2H_5$, —$OCH_3$, alkyl —$C_nH_2$n+1 (where n is an integer from 3-x), —OH, phenyl —$C_6H_5$, naphthyl, or amino acid.

8. The composition comprising a compound of claim 1 having R selected from —$CH_3$ and R1 and R2 independently selected from —H, —$CH_3$, —$C_2H_5$, —$OCH_3$, alkyl —$C_nH_2$n+1 (where n is an integer from 3-x), —OH, phenyl —$C_6H_5$, naphthyl, or amino acid.

9. The composition comprising a compound of claim 1 having R selected from —$C_2H_5$ and R1 and R2 independently selected from —H, —$CH_3$, —$C_2H_5$, —$OCH_3$, alkyl —$C_nH_2$n+1 (where n is an integer from 3-x), —OH, phenyl —$C_6H_5$, naphthyl, or amino acid.

10. The composition comprising a compound of claim 1 having R selected from alkyl —$C_nH_2$n+1 (where n is an integer from 3-x) and R1 and R2 independently selected from —H, —$CH_3$, —$C_2H_5$, —$OCH_3$, alkyl —$C_nH_2$n+1 (where n is an integer from 3-x), —OH, phenyl —$C_6H_5$, naphthyl, or amino acid.

11. The composition comprising a compound of claim 1 having R selected —OH and R1 and R2 independently selected from —H, —$CH_3$, —$C_2H_5$, —$OCH_3$, alkyl —$C_nH_2$n+1 (where n is an integer from 3-x), —OH, phenyl —$C_6H_5$, naphthyl, or amino acid.

12. The pharmaceutical composition comprising at least one compound according to claim 1 and at least one pharmaceutically acceptable carrier.

13. A method of making a compound of claim 1 comprising the following steps:

Converting carbonyl groups on 2-methylnaphthalene to hydroxy groups;

Methylating hydroxy groups to methoxy groups;

Adding an aldehyde group to naphthalene;

Dimerize 1,4-dimethoxy-3-methylnaphthalene-2-carbaldehyde; and

Oxidatively demethylating methoxy groups to carbonyl groups.

* * * * *